United States Patent [19]

Landon

[11] Patent Number: 5,733,742
[45] Date of Patent: Mar. 31, 1998

[54] PRODUCTION OF ANTIBODY FRAGMENTS FROM WHOLE BLOOD

[75] Inventor: John Landon, London, England

[73] Assignee: Therapeutic Antibodies Inc., London, England

[21] Appl. No.: 256,053

[22] PCT Filed: Jun. 3, 1994

[86] PCT No.: PCT/GB94/01210

§ 371 Date: Mar. 10, 1995

§ 102(e) Date: Mar. 10, 1995

[87] PCT Pub. No.: WO94/29348

PCT Pub. Date: Dec. 22, 1994

[30] Foreign Application Priority Data

Jun. 3, 1993 [GB] United Kingdom ............... 9311507
Feb. 10, 1994 [GB] United Kingdom ............... 9402593

[51] Int. Cl.$^6$ ............................ C12P 21/06; C07K 1/22
[52] U.S. Cl. ..................... 435/68.1; 530/413; 530/415
[58] Field of Search ...................... 530/389.8, 390.5, 530/389.2, 387.1, 415, 413; 424/130.1; 435/68.1

[56] References Cited

U.S. PATENT DOCUMENTS

| | | | |
|---|---|---|---|
| 4,061,767 | 12/1977 | Ertel et al. | 424/282 |
| 4,381,295 | 4/1983 | Kung et al. | 424/189.7 |
| 4,603,106 | 7/1986 | Cerami et al. | 435/7.1 |
| 4,684,623 | 8/1987 | Larrick et al. | 514/12 |
| 4,731,244 | 3/1988 | Talle et al. | 424/139.1 |
| 4,742,159 | 5/1988 | Batz et al. | 530/387.1 |
| 4,822,776 | 4/1989 | Cerami et al. | 514/21 |
| 4,849,352 | 7/1989 | Sullivan et al. | 435/69.6 |
| 4,870,163 | 9/1989 | Rubin et al. | |
| 4,918,163 | 4/1990 | Young et al. | 530/387.1 |

FOREIGN PATENT DOCUMENTS

| | | |
|---|---|---|
| 0 350 690 A2 | 1/1990 | European Pat. Off. . |
| 0 351 789 A2 | 1/1990 | European Pat. Off. . |
| 0 355 067 A1 | 2/1990 | European Pat. Off. . |
| 0 460 426 A2 | 12/1991 | European Pat. Off. . |
| 895325 | 7/1989 | South Africa . |
| WO 89/08460 | 9/1989 | WIPO . |
| WO 91/07986 | 6/1991 | WIPO . |
| WO 92/16553 | 10/1992 | WIPO . |
| WO 93/11793 | 6/1993 | WIPO . |

OTHER PUBLICATIONS

Garvey et al. Methods in Immunology p. 256 1977.
Aggarwal et al. Human Tumor Necrosis Factor Production, Purification, and Characterization, Journal of Biological Chemistry, vol. 260, No. 4, pp. 2345–2354, Aug. 21, 1984.
Beutler et al., Purification of Cachectin, A Lipoprotein Lipase–Suppressing Hormone Secreted by Endotoxin–Induced Raw 264.7 Cells, J. Exp. Med., vol. 161, pp. 984–995, May, 1985.
Beutler et al., Identity of Tumour Necrosis Factor and the Macrophage–Secreted Factor Cachectin, Nature, vol. 316, pp. 552–554 Aug., 8, 1985.
Beutler et al., Cachectin and Tumour Necrosis Factor as Two Sides of the Same Biological Coin. Nature, vol. 320, pp. 584–588 Apr. 17, 1986.
Beutler et al., Passive Immunization Against Cachectin/Tumor Necrosis Factor Protects Mice From Lethal Effect of Endotoxin, Science, vol. 229, pp. 869–871, Aug. 30, 1985.
Beutler et al., Fed. Proc. 44, 1704, Activated macrophages Secrete A Novel Lipolytic Polypeptide Hormone, Abstract No. 7565, 1985.
Bone, A Critical Evaluation of New Agents for the Treatment of Sepsis, JAMA, vol. 266, No. 12, pp. 1686–1691, Sep. 25, 1991.
Buttle et al., The Preparation of Fully Active Chymopapain Free of Contaminating Proteinases, Biol. Chem. Hoppe–Seyler, vol. 371, pp. 1083–1088, Nov., 1990.
Buttle et al., Affinity Purification of the Novel Cysteine Proteinase Papaya Proteinase IV, and Papain from Papaya Latex, Biochem J., vol. 261, pp. 469–476, 1989.
Brennan et al., Inhibitory Effect of TNFα Antibodies on Synovial Cell Interleukin–1 Production in Rheumatoid Arthritis, The Lancet, pp. 244–247, Jul. 29, 1989.
Carswell et al., An Endotoxin–Induced Serum Factor that Causes Necrosis of Tumors, Proc. Nat. Acad. Sci., vol. 72, No. 9, pp. 3666–3670, Sep., 1975.
Cerami et al., Weight Loss Associated with an Endotoxin–Induced Mediator from Perintoneal Macrophages: The Role of Cachectin (Tumor Necrosis Factor), Immunology Letters, vol. 11, pp. 173–177, 1985.
Elliott et al., Treatment of Rheumatoid Arthritis with Chimeric Monoclonal Antibodies to Tumor Necrosis Factorα, Arthritis & Rheumatism, vol. 36, No. 12, pp. 1681–1690, Dec., 1993.
Erikaku et al., Bioluminescent Immunoassay Using a Monomeric Fab'–Photoprotein Aequorin Conjugate, Biochemical and Biophysical Research Communications, vol. 174, No. 3, pp. 1331–1336, Feb. 14, 1991.
Feldmann et al., Evaluation of the Role of Cytokines in Autoimmune Disease: The Importance of TNFα in Rheumatoid Arthritis, Progress in Growth Factor Research, vol. 4, pp. 247–255, 1992.
Fransen et al., Molecular Cloning of Mouse Tumour Necrosis Factor cDNA and its Eukaryotic Expression, Nucleic Acids Research, vol. 13, No. 12, pp. 4417–4429, 1985.
Glauser et al., Septic Shock: Pathogenesis, The Lancet, vol. 338, pp. 732–736, Sep. 21, 1991.
Goldstein et al., A Randomized Clinical Trial of OKT3 Monoclonal Antibody for Acute Rejection of Cadaveric Renal Transplants, The New England Journal of Medicine, vol. 313, No. 6, pp. 337–342, Aug. 8, 1985.

(List continued on next page.)

Primary Examiner—Lila Feisee
Assistant Examiner—Phillip Gambel
Attorney, Agent, or Firm—Finnegan, Henderson, Farabow, Garrett and Dunner, L.L.P.

[57] ABSTRACT

A method of preparing polyclonal immunoglobulin Fab fragments comprising cleaving immunoglobulin molecules, characterised in that the said cleavage is carried out on immunoglobulins in blood, serum or plasma in a closed, sterile environment.

9 Claims, 12 Drawing Sheets

OTHER PUBLICATIONS

Haranaka et al., Purification and Partial Amino Acid Sequence of Rabbit Tumor Necrosis Factor, Int. J. Cancer, vol. 36, pp. 395–400, 1985.

Hinds, Monoclonal Antibodies in Sepsis and Septic Shock, BMJ, vol. 304, pp. 132–133, Jan. 18, 1992.

Hotez et al., Lipoprotein Lipase Suppression in 3T3–L1 Cells by a Haematoprotozoan–Induced Mediator from Peritoneal Exudate Cells, Parasite Immunology, vol. 6, pp. 203–209, 1984.

Lamoyi et al., Preparation of F(ab')$_2$ Fragments from Mouse IgG of Various Subclasses, Journal of Immunological Methods, vol. 56, No. 2, pp. 235–243, Jan. 28, 1983.

Kawakami et al., Lipoprotein Lipase Suppression in 3T3–L1 Cells by an Endotoxin–Induced Mediator from Exudate Cells, Proc. Natl. Acad. Sci., vol. 79, pp. 912–916, Feb., 1982.

Kawakami et al., Studies of Endotoxin–Induced Decrease in Lipoprotein Lipase Activity, J. Exp. Med., vol. 154, pp. 631–639, Sep., 1981.

Liang et al., Production and Characterization of Monoclonal Antibodies Against Recombinant Human Tumor Necrosis Factor/Cachectin, Biochemical and Biophysical Research Communications, vol. 137, No. 2, pp. 847–854, 1986.

Mahoney, Jr., et al., Lipopolysaccharide–Treated Raw 264.7 Cells Produce a Mediator that Inhibits Lipoprotein Lipase in 3T3–L1 Cells, The Journal of Immunology, vol. 134, No. 3, pp. 1673–1675, Mar., 1985.

Maini et al., TNF–α in Rheumatoid Arthritis and Prospects of Anti–TNF Therapy, Clinical and Experimental Rheumatology 11, Suppl. 8: pp. S173–S175, 1993.

Mannel et al., Macrophages as a Source of Tumoricidal Activity (Tumor–Necrotizing Factor), Infection and Immunity, vol. 30, No. 2, pp. 523–530, Nov., 1980.

Mannel et al., Inhibition of Nonspecific Tumoricidal Activity by Activated Macrophages with Antiserum Against a Soluble Cytotoxic Factor, Infection and Immunity, vol. 33, No. 1, pp. 156–164, Jul., 1981.

Nawa, Tissue–specific Generation of Two Preprotachykinin mRNAs from One Gene by Alternative RNA Splicing, Nature vol. 312, 20/27, pp. 729–734, Dec., 1984.

Negussie et al., Detection of Plasma Tumor Necrosis Factor, Interleukins 6, and 8 during the Jarisch–Herxheimer Reaction of Relapsing Fever, J. Exp. Med., vol. 175, pp. 1207–1212, May, 1992.

Pekala et al., Selective Inhibition of Synthesis of Enzymes for de novo Fatty Acid Bio–Synthesis by an Endotoxin–Induced Mediator from Exudate Cells, Proc. Natl. Acad. Sci., vol. 80, pp. 2743–2747, May, 1983.

Pennica et al., Human Tumour Necrosis Factor: Precursor Structure, Expression and Homology to Lymphotoxin, Nature, vol. 312, 20/27, pp. 724–729, Dec., 1984.

Piquet et al., Evolution of Collagen Arthritis in Mice is Arrested by Treatment with Anti–Tumour Necrosis Factor (TNF) Antibody or a Recombinant Soluble TNF Receptor, Immunology, vol. 77, pp. 510–514, 1992.

Rouzer et al., Hypertriglyceridemia Associated with Trypanosoma Brucei Brucei Infection in Rabbits: Role of Defective Triglyceride Removal, Molecular and Biochemical Parasitology, vol. 2, pp. 31–38, 1980.

Schnabel, The Magic Bullet that Burst the Bubble, New Scientist, Sep. 26, 1992, pp. 31–35.

Shim et al., The Nature of Endotoxin–Induced Tumor Necrosis Factor, Korean J. Biochem., vol. 11, pp. 1–9, 1979.

Smith et al., An Affinity Purified Ovine Antivenom for the Treatment of Vipera Berus Envenoming, Toxicon, vol. 30, No. 8, pp. 865–871, 1992.

Teng et al., Protection Against Gram–Negative Bacteremia and Endotoxemia with Human Monoclonal IgM Antibodies, Proc. Natl. Acad. Sci., vol. 82, pp. 1790–1794, Mar., 1985.

Tracey et al., Anti–Cachectin/TNF Monoclonal Antibodies Prevent Septic Shock during Lethal Bacteraemia, Nature, vol. 330, pp. 662–664, Dec., 1987.

Williams et al., Anti–Tumor Necrosis Factor Ameliorates Joint Disease in Murine Collagin–Induced Arthritis, Proc. Natl. Acad. Sci., vol. 89, pp. 9784–9788, Oct. 1992.

Williamson et al., Human Tumor Necrosis Factor Produced by Human B–Cell Lines: Synergistic Cytotoxic Interaction with Human Interferon, Proc. Natl. Acad. Sci., vol. 80, pp. 5397–5401, Sep., 1983.

Ziegler, Treatment to Gram–Negative Bacteremia and Shock with Human Antiserum to a Mutant *Escherichia coli*, The New England Journal of Medicine, vol. 307, No. 20, pp. 1225–1230, Nov. 11, 1982.

SCRIP No. 1818/19, Celltech Completes Anti–TNF Study, Products Articles, PJB Publications Ltd., May 7/11, 1993.

SCRIP No. 1843, Centocor's Anti–TNF MA$_b$ for Crohn's Disease, Products Articles, PJB Publications Ltd. Aug. 3, 1993.

Raikher et al., Isolation of Fab–and Fc–Fragments of Immunoglobulins Without Column Chromatography, Chemical Abstracts, vol. 102, No. 5, Abstract No. 43971j, Feb. 4, 1985.

ACTIVATION AND COUPLING TO SEPHAROSE

PRODUCTION OF ANTIBODY FRAGMENTS FROM WHOLE BLOOD

This application is a §371 National Phase Application based upon PCT/GB94/01210, filed Jun. 3, 1994 published as WO94/01210 Dec. 22, 1994.

The present invention relates to the production and use of immunoglobulin Fab fragments.

Antibodies are formed as part of the immune response to a microorganism or foreign macromolecule. They are immunoglobulins (Ig) and are used extensively in clinical practice for the diagnosis, monitoring, prevention and treatment of an increasing number of diseases.

The basic unit from which all antibody molecules are formed was elucidated by Porter (1959) *Biochem J.* 73, 119–126, using specific proteolytic enzymes. The most important of the immunoglobulins, IgG, comprises two heavy and two light chains with the former being coupled at their hinge region by disulphide linkages. Cleavage with papain above these linkages releases two antibody binding fragments (Fab) and a crystalline fragment (Fc) as shown in FIG. 1. Cleavage with pepsin, below the hinge results in a somewhat smaller Fc fragment and a single $F(ab')_2$ fragment with two binding sites as shown in FIG. 1. Each Fab fragment contains both a light chain and part of a heavy chain, and includes the sequences responsible for specific binding to a microorganism or foreign macromolecule. The Fc consists of the remainder of the two heavy chains; this is the site to which complement, macrophages and polymorphonuclear white blood cells can bind. The two heavy chains (but not the light chains) are different for each class of antibody ie IgG, IgM, IgA and IgE. IgG is the dominant circulating immunoglobulin in terms of concentration. It consists of a single basic immunoglobulin unit and, characteristically, has a high affinity for its specific antigen. Further details of antibody structure and function are disclosed in Roitt (1991) *Essential Immunology*, 7th Edition, Blackwell Scientific Publications, Oxford.

One of the major problems in preparing immunoglobulins and immunoglobulin fragments for therapeutic use is the possibility of bacterial contamination during manufacture of the product. This risk applies equally to the processing of polyclonal antisera and monoclonal antibodies. The problem is not eliminated by sterile filtration of the end-product because, while this may remove the bacteria themselves, it does not remove the soluble toxins which they may have released at an earlier stage.

The risk to the patient of bacterial and toxin contamination can be obviated by careful testing of the end-product both in vitro (LAL test) and in vivo (rabbits). However, it is clearly preferable that the primary contamination should be avoided, at the very least because this would save the considerable expense of discarding batches of material which did not meet the very stringent quality control parameters. Contamination of product is likely to occur whenever it is transferred from one sterile environment to another, for example from the vessel in which the blood is collected to that in which the initial protein purification is performed.

Classically, the production of Fab fragments relies on papain digestion. The digestion procedure involves incubation of a solution of papain with a substantially pure preparation of immunoglobulins under defined conditions of pH, temperature and co-factors (such as cysteine and ethylene diamine tetra-acetic acid; EDTA) which serve to activate the enzyme and bind its inhibitors, respectively. Although the need to purify the immunoglobulin fraction from blood, plasma or serum before digestion with papain is time consuming and may result in significant losses and impairment of their ability to bind and neutralise antigens, the application of papain to blood, serum or plasma has never been described.

SUMMARY OF THE INVENTION

One aspect of the invention provides a method of preparing polyclonal immunoglobulin Fab fragments comprising cleaving immunoglobulin molecules, characterised in that the cleaving is carried out on immunoglobulins in blood, serum or plasma.

Preferably, the cleaving is carried out, and the Fab fragments are subsequently isolated, in a closed, sterile environment.

The cleaving is conveniently carried out by contacting papain or a catalytic fragment or mutant thereof, or an equivalent enzyme, with the blood. However, it may alternatively be carried out by any other means, since the point of the invention is to cleave the immunoglobulin in blood, serum or plasma; how the cleavage is achieved is immaterial and unrelated to the fact that the cleavage is carried out in blood, serum or plasma.

It is preferred if whole blood is used.

By "equivalent enzyme", we simply mean an enzyme which cleaves Fab fragments from immunoglobulins in substantially the same way as papain. For example, chymopapain is an equivalent enzyme. The preparation of fully active chymopapain, free of contaminating proteinases, is disclosed in Buttle et al (1990) *Biol. Chem. Hoppe-Seyler* 371, 1083–1088 and incorporated herein by way of reference. See in particular the Materials and Methods section on pages 1084 to 1085.

For convenience, we shall generally use the term "blood" hereinafter to mean "blood, serum or plasma", unless the context indicates otherwise.

In order to eliminate substantially the possibility of contamination of the blood, or any Fab fragment derived therefrom, the number of transfers between sterile containers should be reduced, and preferably the blood is collected through a sterile needle into a sterile container, and all subsequent steps, including sterile filtration and ampouling of the product take place within the same sterile environment.

Conveniently, the sterile containers are interconnected via tubes fitted with suitable locks and valves.

Thus, one preferred embodiment of the invention provides a method of preparing immunoglobulin Fab fragments from blood in a closed, sterile environment comprising (1) immunizing an animal, (2) bleeding the animal aseptically into a sterile, pyrogen-free container, (3) contacting the whole blood with papain or an equivalent enzyme and (4) removing cellular components and much of the Fc.

The animal to be immunized may be a sheep, a goat, a horse or other mammal. It is preferable that the animal is a sheep, and that it is free of scrapie and zoonotic viruses.

The immunogen may be a polypeptide, a polypeptide fragment, a synthetic peptide, a polysaccharide, a glycoprotein, a hapten or any other molecule capable of giving rise to a humoral immune response. It is preferable that peptides and haptens are conjugated to carrier molecules such as keyhole limpet haemocyanin or albumin.

It is further preferred that the immunogen is administered with an adjuvant such as Freund's complete adjuvant or Freund's incomplete adjuvant or others well known in the art.

In one embodiment of the invention the immunogen is recombinant tumour necrosis factor α (TNFα).

In a further embodiment of the invention the immunogen is a tricyclic antidepressant, for example nortriptyline.

It is preferred that the animal is immunized according to a set schedule, with amounts of immunogen selected on the basis of dose response studies. A specific immunization schedule is given in the Examples. Once adequate circulating antibody levels of at least 1 g/l, more preferably 2 g/l and still more preferably 3 g/l or more are achieved following immunization, the animal is bled.

The animal is bled through a sterile needle and sterile tube into a sterile container. Conveniently 19 or 21 gauge needles and tubes are used, but a wider gauge may be desirable when faster bleeding is required.

Typically 500 ml of blood is collected into a blood pack, preferably a double pack.

It is preferred that 10 ml of blood is taken per kg of body weight of animal, but this may vary depending on the titre of the specific antibodies present in the blood.

The sterile container contains a known amount of papain, the amount dependent on the amount of whole blood to be digested.

Papain is commercially available from, for example, E. Merck Inc, Darmstadt, Germany and other suppliers of biochemical reagents.

It is preferred that the papain is substantially pure. Substantially pure papain can be prepared by an affinity purification method as described by Buttle et al (1989) *Biochem. J.* 261, 469–476.

It is also preferred if substantially pure chymopapain, as disclosed by Buttle et al (1990) *Biol. Chem. Hoppe-Seyler* 371, 1083–1088, is used.

The amount of papain used to digest whole blood will vary according to the purity and specific activity of the papain. It is preferred that between 0.5 g and 2.5 g of Merck 6000 USP-U/mg papain is used per 100 ml of blood, most preferably 1.5 g/100 ml.

It is most preferable to use L-cysteine and EDTA, disodium salt in combination with papain in order to enhance the activity of the papain, and to chelate inhibitors of papain. Other sulphydryl agents may be used instead of L-cysteine.

L-cysteine is added at a concentration of between 0.5 g and 2 g per 100 ml of blood, preferably at about 1 g per 100 ml blood.

EDTA, disodium salt, is added at a concentration of between 0.5 g and 3.0 g per 100 ml of blood, preferably at a concentration of about 1.5 g per 100 ml of whole blood.

Papain digestion is usually carried out for between 3 and 5 hours, and at a temperature of 37° C. It is preferred that the digestion is carried out with pH between 6 and 8; pH 7.5 is most preferred. Once digestion of the whole blood has been done, the cellular components are removed by centrifugation. It is desirable to inactivate papain at the end of the digestion period by the addition of iodoacetamide, a cysteine proteinase inhibitor. Other cysteine proteinase inhibitors may be used. Incubation for longer than 5 hours, using 1.5 g of papain per 100 ml, may lead to undesirable haemolysis.

At this stage of the process, the remaining mixture will contain (1) specific Fab directed against the immunogen of interest; (2) non-specific Fab directed against numerous other epitopes and of no interest; (3) all other serum proteins (including albumin but excluding intact 1 g) and other contaminants; and (4) inactivated papain.

In a further preferred embodiment of the invention the papain is immobilized on a support.

Although "liquid phase" digestion can be carried out as described above, in some circumstances it is desirable that the papain is immobilized on a support. Suitable supports are well known particularly in the field of column chromatography and include agarose, polyacrylamide, agarose/polyacrylamide co-polymers, dextran, cellulose, polypropylene, polycarbonate, glass, paper or the like. It is preferred that the solid support is cellulose and that the papain is chemically cross-linked thereto.

The solid support may take the form of granules or powder or gel that is suitable for use in column chromatography.

The papain may be joined to the solid support in a variety of ways.

A straightforward way to chemically cross-link papain to a solid support is if the support is previously activated with cyanogen bromide (CNBr) as disclosed by Axen et al (1967) *Nature* 258, 598–599. CNBr activated supports react rapidly at pH 8–9 with free amino groups in the papain to give a covalently linked product. In this embodiment it is desirable if the solid support is agarose, and the CNBr-activated agarose is CNBr-activated Sepharose 6MB available from Pharmacia Inc.

Although it is convenient if the solid support is in a form suitable for preparation into columns such as those used for column chromatography, it will be appreciated that the papain can be used in the "solid phase" in other situations.

Thus, in a further embodiment the solid support is formulated into a substrate such as a disc or sinter or floor of a suitable container.

In a further embodiment, the IgG-containing material (blood, serum or plasma) is delivered to the solid support in batches. Thus the solid support may be placed in a centrifuge tube and the IgG-containing material applied. In order to remove the papain from contact with the IgG, the tube is centrifuged and the solid support precipitated. In all of these embodiments the solid support containing the papain can be washed and reused with further amounts of IgG-containing material.

It is preferred if the support is cellulose. It is further preferred if the cellulose has between 0.1 mg and 20 mg of papain per g immobilized thereon.

Use of immobilised papain may be particularly advantageous since the immobilized enzyme can be reused, and the use of a potentially toxic enzyme inhibitor to stop the enzymatic reaction can be avoided, as the immobilized enzyme can be simply removed physically.

A separate aspect of the invention provides a method of making Fab fragments comprising contacting IgG with papain or an equivalent enzyme characterised in that the papain or an equivalent enzyme is immobilised on a solid support.

It is preferred if the IgG is provided as solution at a greater concentration than is found in serum. Solutions of partially purified IgG can be prepared by, for example, sodium sulphate precipitation of serum as described in more detail in the Examples.

In a still further embodiment an additional step of substantially purifying the specific Fab fragments by binding the said fragments to their ligand, removing the unbound material, and separating the said fragments from the said ligand is performed.

Although this step can be performed when the papain has been used in the liquid phase or used when immobilized to a support, it is preferred if it is used when the papain has been used in the liquid phase.

Further embodiments are described below wherein plasma or serum is used in similar methods.

Thus, the specific activity of the Fab fragment may then be increased by affinity purification. In a preferred embodiment the polyclonal Fab fragments are passed over an inert matrix to which has been bound the Fab fragment-specific ligand. Specific Fab molecules in the mixture bind to the ligand while the remainder, accounting for up to 95% of the total Fab fragment present, pass through and are discarded. Consequently, such a process may reduce the effective amount of proteins to be used in a therapeutic dose, by as much as 95%. These purified Fab are then typically either lyophilised or liquid filled into ampoules depending on their intended use.

Of course, in order for the affinity purification step to be carried out, the specific ligand may comprise the immunogen, or at least the smallest fragment thereof that binds the said Fab fragment, or it may be a synthetic peptide containing the epitope recognised by the said Fab fragment, or it may comprise the said epitope in any other polypeptide or it may comprise the hapten or analogue thereof.

There are many advantages of a specific affinity chromatography step. This step eliminates Fab fragments and antibody to irrelevant epitopes, contaminating proteins (such as albumin and papain), and other potentially toxic molecules. The smaller the amount of a protein given to a patient, and the greater its purity, the less likely it is to cause allergic or other side effects.

This approach is much superior to the use of non-specific affinity chromatography with protein A or G which purifies all antibodies. Furthermore protein A or G supports are inappropriate in the present context because they bind to the Fc part of the immunoglobulin. The production of substantially purified specific Fab without the 80% or more of non-specific Fab greatly reduces the amount of foreign protein required for various applications including therapy.

Alternatively, or additionally, to affinity purification, ion-exchange chromatography can also be used.

In certain circumstances, for example when plasma or serum, rather than whole blood has been stored, it is desirable to digest the plasma or serum, rather than whole blood with papain. However, digestion of whole blood is preferred.

A further embodiment of the invention provides a method of preparing immunoglobulin Fab fragments in a closed, sterile environment comprising (1) immunizing an animal, (2) bleeding the animal aseptically into a sterile, pyrogen-free container, (3) preparing plasma from the blood, (4) contacting the plasma with papain or an equivalent enzyme and optionally (5) substantially purifying the specific Fab fragments by binding the said fragments to their ligand, removing the unbound material and separating the said fragments from the said ligand.

Plasma may be prepared from the whole blood by adding between 0.5 g and 2 g (preferably 1 g) EDTA (disodium salt) per 100 ml of whole blood which prevents the blood clotting. The blood is then centrifuged at 2500×g for 30 minutes at 4° C. to separate the plasma from the blood cells.

Papain may be added to the plasma at between 1.0 g and 5.0 g (preferably 2.5 g) per 100 ml of starting whole blood, and digestion may be carried out for up to 24 hours, at a temperature of 37° C. It is preferred that the digestion is carried out with pH between 6 and 8; pH 7.5 is most preferred. Papain may be inhibited by iodoacetamide at the end of the digestion period. It is preferred that EDTA and L-cysteine are present during papain digestion, but is not essential.

The specific Fab are affinity-purified as disclosed.

A further embodiment of the invention provides a method of preparing immunoglobulin Fab fragments in a closed, sterile environment comprising (1) immunizing an animal, (2) bleeding the animal aseptically into a sterile pyrogen-free container, (3) preparing serum from the blood, (4) contacting the serum with papain or an equivalent enzyme and optionally (5) substantially purifying the specific Fab fragments by binding the said fragments to their ligand, removing the unbound material, and separating the said fragments from the ligand.

Serum may be prepared by allowing whole blood to stand for 1 hour at room temperature and then centrifuging at 2500×g for 30 minutes at Papain, between 0.5 g and 3.0 g (preferably 1.5 g), EDTA (disodium salt) between 0.25 g and 1.0 g (preferably 0.5 g) and L-cysteine, between 0.15 g and 0.6 g (preferably 0.3 g) may be added to the serum for each 100 ml of whole blood, and digestion may be carried out for up to 24 hours, and at a temperature of 37° C. It is preferred that the digestion is carried out with pH between 6 and 8; pH 7.5 is most preferred. It is also preferred if EDTA and L-cysteine are present during papain digestion, but it is not essential. The specific antibodies are then affinity purified as disclosed above.

It has been found that the same proportions of EDTA (disodium salt), L-cysteine and papain to blood (or plasma or serum) are useful for generating Fab fragments when at least 50 ml; 100 ml; 500 ml; 1000 ml; 2000 ml or 3000 ml of blood (or plasma or serum) are used as the source of immunoglobulin.

For the specific case of nortriptyline-specific antibodies, the animal is immunized with nortriptyline bound to a carrier, and which may be in combination with an adjuvant, and is subsequently bled.

Fab fragments are generated using any of the methods of the invention, and affinity purification of the said drug-specific Fab fragments is performed using an affinity column to which is bound nortriptyline.

A nortriptyline affinity column is readily produced by attaching nortriptyline to Sepharose 4B (Trademark; Pharmacia LKB Biotechnology), and is used by methods well known in the art. Specific Fab fragments bind to this column and may be eluted from the affinity column by changing the pH, ionic strength or nature of the solvent.

Thus in one embodiment of the invention nortriptyline is used as an immunogen and Fab fragments which bind nortriptyline are affinity purified using nortriptyline as a ligand.

For the specific case of TNFα-specific antibodies, the animal is immunized with TNFα, preferably rhTNFα, or a peptide representing a TNFα epitope thereof, which may be in combination with an adjuvant, and is subsequently bled. Fab fragments are generated using any of the methods of the invention and affinity purification of the said cytokine-specific Fab fragments is performed using an affinity column to which is bound TNFα or a peptide representing an anti-TNFα Fab fragment binding epitope thereof.

By "rhTNFα" we mean recombinant DNA-derived human TNFα.

A TNFα affinity column is readily produced by attaching TNFα, preferably rhTNFα, to a CNBr-activated Sepharose 4B column using methods well known in the art. Specific Fab fragments bind to this column and may be eluted by changing the pH, ionic strength or nature of the solvent.

Thus, in one embodiment of the invention TNFα is used as an immunogen and Fab fragments which bind TNFα are affinity purified using TNFα as the ligand.

A further aspect of the invention provides Fab fragments reactive towards TNFα.

Fab fragments produced from papain digestion of whole blood, plasma or serum may be useful in many areas of medicine, dependent on the specificity of the said Fab fragments. Thus, such Fab fragments may be used as anti-venoms if the immunogen is a venom, or analogue thereof, or as anti-toxins if the immunogen is a toxin, or analogue thereof.

It is preferred if the Fab fragments of the invention are used to treat human patients and, in particular, we have found Fab fragments reactive towards TNFα useful in treating septic shock in humans.

A further aspect of the invention provides a method of clotting blood comprising placing blood into a container and moving said container so that the blood platelets are damaged by contacting an inner surface of the container. When platelets are damaged the blood begins to clot. Suitably, greater than 70% of the blood is clotted by the process. Preferably greater than 80% or greater than 95% is clotted. Clotting can be readily observed by visual inspection.

We have determined a number of basic conditions which allow clotting without the necessity to resort to the addition of coagulation additives:

1. Sterile blood collection to occur in less than 10 minutes to optimise platelet and Factor VIII yield and activity.
2. Storage of collected blood at 20°–24° C. to promote maximum platelet and Factor VIII activity.
3. Rapid activation of the coagulation cascade by continuous exposure of Hageman Factor (Factor XII) to the surface of the collection vessel.
4. Post collection rapid maximised damage to platelets to induce the release of large amounts of platelet phospholipids.
5. The presence of $Ca^{2+}$ ions either indigenously or from the glass bottles.
6. If plastics are used it is essential to ensure the absence of chelating agents, and substances within the plastic which may interfere with any of the steps of the clotting cascade.

In a preferred method the blood is collected in a sterile, pyrogen-free cylindrical container of glass or plastic. Conveniently, conventional blood bags are used and placed inside a cylindrical bottle. The container is rotated at between 5 and 25 rpm. Preferably the container is between 10 and 20 cm in diameter. A diameter of about 12 cm is preferred and rotation speed of between 10 rpm and 20 rpm, most preferably 12 rpm. It is preferred if the container is rotated at between 4° and room temperature for about 20 to 30 min. Room temperature of 20° C. to 25° C. is preferred. Clearly, if the rotation speed is too great frothing will occur, and if rotation is too slow, then the platelets are not damaged and clotting will not occur very quickly.

The advantages of the present method (which we call "speed-clotting" or "roll-bottle" method) over the prior art method of leaving blood at 4° for 12 h–16 h is that the likelihood of bacteria or other microorganisms, which are present in the blood, reproducing is greatly reduced.

A further aspect of the invention provides a process for preparing Fab fragments comprising (i) clotting blood by the "speed clotting" method described above, (ii) preparing an immunoglobulin fraction, (iii) contacting the said immunoglobulin with papain or a functionally equivalent enzyme and (iv) a further step to substantially purify the Fab fragment.

An immunoglobulin fraction can be prepared by well known methods from the supernatant produced after clotting has occurred.

Sodium or ammonium sulphate precipitation is preferred.

The Fab fragment can be substantially purified by standard chromatography steps. Cation exchange chromatography is particularly preferred.

The process of producing Fab fragments described using the "speed clotting" method is particularly suited for the veterinary market because of its cost-savings compared with other Fab production methods. Because of the shorter process times involved antiserum can be prepared easily within a working day from a large number of immunized animals, for example, blood from 120 sheep can be processed in a single day.

It is particularly preferred if the above process using "speed clotting" is performed in a sterile, pyrogen-free, closed system.

The invention will now be described with reference to the following Examples and Figures wherein

EXAMPLE 1

Figure 1:
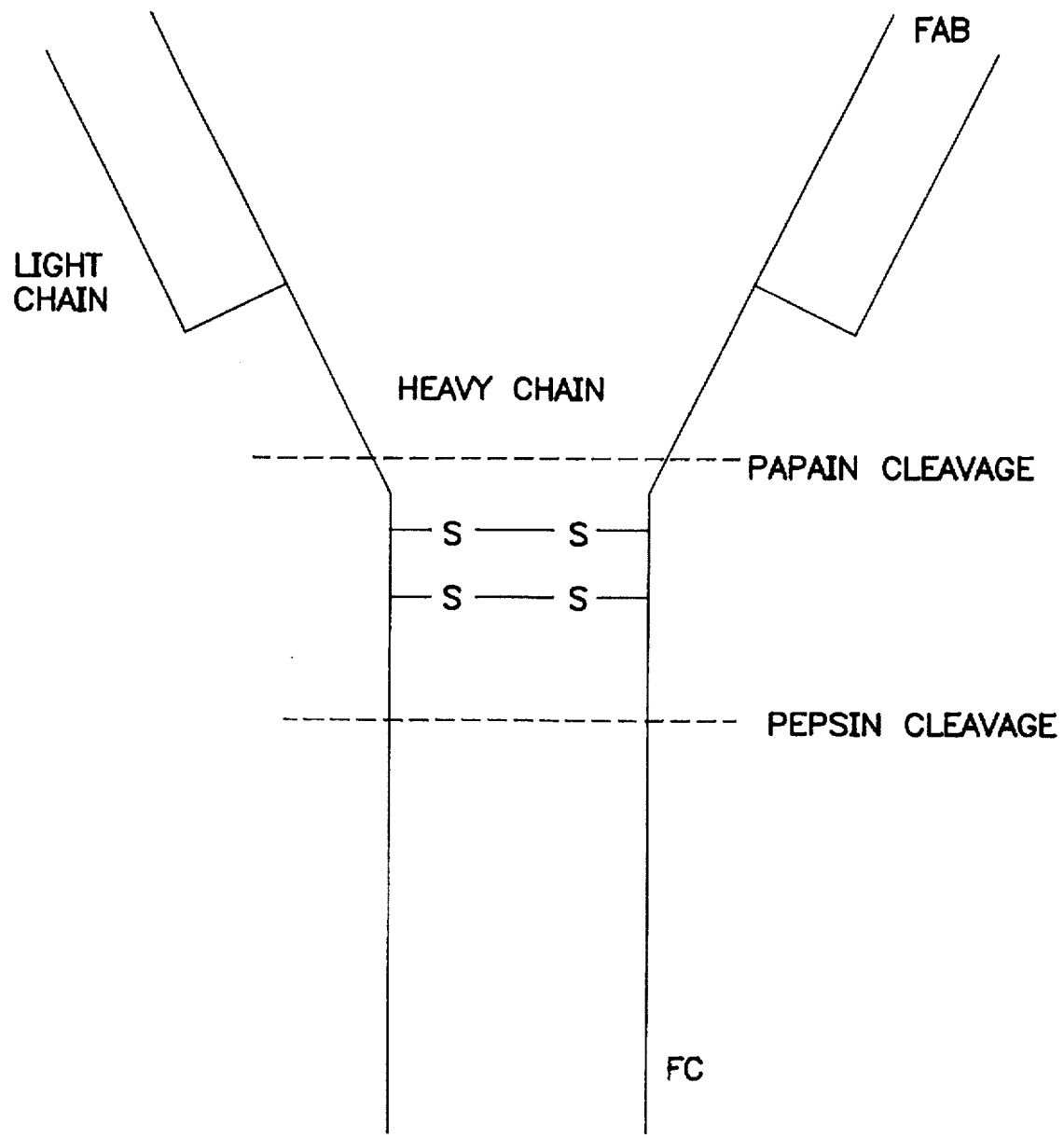
FIG. 1 is a diagrammatic representation of the structure of an antibody molecule.

Preparation of TNFα Immunogen for immunizing sheep

Procedure

Preparation of vials containing active TNFα immunogen

The vials should be new, dust free and treated with sialinating fluid 48 hours in advance to prevent adhesion of the immunogen to the vials. Fresh sialinating solution needs to be made up every 24 hours.

Sialinating is carried out in the following way a) In a fume hood line up vials in a metal tray;

b) Make up sialinating solution to the manufacturer's instructions. Dilute to a 0.1% solution. Note 0.2% solution is achieved by 99 parts water to 1 part AQUA-SIL (Trademark). Stir constantly. Flood the vials in the solution. Then allow to air dry for a minimum of 24 hours.

Remove TNFα from the 4° C. store and allow to equilibrate at room temperature for a minimum of 30 minutes.

The total amount of TNFα for a single monthly immunization for the entire flock is weighed out into a sterile 150 ml Sterilin (Trademark) flask using the balance. The necessary calculations are given under the heading "Calculations involved in immunogen preparation" below. This is represented as E in the calculations described below. Any spare immunogen prepared may be stored and used at a later date.

The immunogen is then dissolved in 0.9% saline. The solution is then mixed by end-over-end rotation for a minimum of 30 minutes. The amount of saline used is F as described below.

The prepared immunogen solution is aliquoted into vials using sterile pipettes and a Pipetteman (Trademark) device.

Calculations involved in the immunogen preparation

Each vial should contain sufficient immunogen for 3 sheep. Therefore divide the total number of sheep for immunization (A) by three and round up to the next whole number.

$A/3 = B$ eg $49/3 = 16.33$ therefore 17

The amount of TNFα to be weighed out is therefore 3B multiplied by the amount of immunogen needed per sheep (C).

$(3*B)C = D$ eg If preparing immunizing dose of 80 μg
per sheep$(3*17)80 = 4080$ μg $= 4.08$ mg The amount of TNFα compared with the salt content, which can vary from batch to batch, has to be taken into account when weighing immunogen.

$(D/\text{percentage } TNF\alpha \text{ in supplied material})100 = E$
eg If the supplied material contains 95% salt
and therefore 5% $TNF\alpha (4.08/5)100 = 81.6$ mg The weighed out immunogen is then dissolved in the appropriate amount of 0.9% saline, which is calculated by multiplying the number of vials to be used by 4. Each vial should contain 4 ml of saline.

$B*4 = F$ eg $17*4 = 68$ ml

EXAMPLE 2

Immunization, sample and bleed protocol for anti-TNFα sheep

The table gives a year's fortnightly schedule of the immunization dose administered, the volume of bleed and the processing of individual samples or pooled samples for the production sheep immunized against TNF-α.

A sample is taken from each animal prior to primary immunization. This level is the background level in each sheep.

The following definitions are used:

I: Primary Immunization

R#: Reimmunization number post primary immunization

Sample: 5–10 ml blood sample from each animal for assessment of titre

Bleed: 10 ml blood taken per kg of body weight

IS: Individual sample for assessment of the individual performance

P: Pooling of bleeds from all individuals

| Week Number | Immunization Number | Dose (μg) | Sample or Bleed | Sample Processing |
|---|---|---|---|---|
| 0 | I | 160 | | |
| 2 | | | | |
| 4 | R1 | 80 | | |
| 6 | | | Sample | IS |
| 8 | R2 | 80 | | |
| 10 | | | | |
| 12 | R3 | 80 | | |
| 14 | | | | |
| 16 | R4 | 80 | | |
| 18 | | | | |
| 20 | R5 | 80 | | |
| 22 | | | Sample | IS |
| 24 | R6 | 80 | | |
| 26 | | | Bleed | P |
| 28 | R7 | 80 | | |
| 30 | | | Bleed | P |
| 32 | R8 | 80 | | |
| 34 | | | Bleed | P |
| 36 | R9 | 80 | | |
| 38 | | | Bleed | P |
| 40 | R10 | 80 | | |
| 42 | | | Bleed | P |
| 44 | R11 | 80 | | |
| 46 | | | Bleed | P |
| 48 | R12 | 80 | | |
| 50 | | | Bleed | P |
| 52 | R13 | 80 | | |

EXAMPLE 3

Purification of chymopapain

The method of Buttle et al (1990) *Biol. Chem. Hoppe-Seyler* 371, 1083–1088 was used to purify chymopapain.

Dried papaya latex (14 g) was added to water, 0° C., to 20% (w/v) in a contained environment, and stirred for 1 h. HCl (1M) was added to pH 1.5, with stirring, over a 1 h period. The preparation was centrifuged (12000×g, 30 rain, 4° C.) and the pellet discarded. NaOH (1M) was added to the supernatant at 0° C., with stirring, to pH 7.0. The resulting mixture was then centrifuged as above and the pellet was discarded. The supernatant was dialysed against two changes of 30 vol. of water at 4° C.

The S-Sepharose column was run using the FPLC system at a flow rate of 10 ml/min. It was equilibrated in potassium phosphate buffer (50 mM with respect to K$^+$) containing 1 mM EDTA, pH 7.2. The dialysed supernatant (above) was filtered (0.2 μm) and applied to the column, which was then washed with the potassium phosphate buffer until $A_{280}$ returned to baseline. A gradient (0.175 mM K⁺/ml) up to 0.6M [potassium] phosphate with 1 mM EDTA, pH 7.2, was applied, and fractions (25 ml) were collected. The column was then washed with potassium phosphate buffer (1M K⁺) and re-equilibrated under the starting conditions. Fractions containing chymopapain (determined immunologically), eluting at approximately 200 mM K⁺, with high amidase activity, were pooled.

Ethanediol was added to the pool to 33% (v/v), followed by cysteine to 5 mM. The solution was mixed thoroughly, allowed to stand at 4° C. for 20 min, and applied to the Sepharose-ECH-Ala-PheSc column at a flow rate of 10 ml×cm$^{-2}$×h$^{-1}$. The column was washed with 7 bed vol. of 50 mM sodium phosphate, 1 mM EDTA, pH 6.8 in 33% (v/v) ethanediol. Active enzyme was then eluted in 3 bed vol. of 50 mM sodium acetate, 3% (v/v) ethanediol, pH 4.5, containing 10 mM $HgCl_2$. Fractions (25 ml) were collected throughout. The affinity column was finally re-equilibrated in the sodium phosphate, ethanediol, pH 6.8 buffer, and stored at 4° C.

Fractions active against $Bz-DL-Arg-NHPhNO_2$ were combined, dialysed against water, and either stored at 4° C., or freeze-dried.

Materials and Methods

Dried papaya latex ("papain") was obtained from J. E. Siebel Sons Co. Inc., 4055 West Peterson Ave., Chicago, Ill. 60646, USA. ECH Sepharose 4B, the S-Sepharose High Performance 35/100 Biopilot prepacked column and other equipment for chromatography were from Pharmacia LKB Biotechnology, Milton Keynes, UK. Compound E-64 and iodoacetic acid (99%) were from Sigma Chemical Co. Ltd., Dorset BH17 7 NH, UK. The pH electrode was type GK 2401 from Radiometer, Crawley RH10 2PY, UK., who also supplied the pH standard buffers at pH values 1.09, 4.01 and 7.00 (25° C.).

Typical purification results are shown in Table 1.

Enzymatic activity hydrolysing $Bz-DL-Arg-NHPhNO_2$ is given in nKat. Since the substrate is also hydrolysed by papain and papaya proteinase III, the yield of activity is an underestimate of the yield of chymopapain, n.d. =not determined.

EXAMPLE 4
Purification of papain

The method of Buttle et al (1989) Biochem. J. 261, 469–476 was used to purify papain.

A column (4 ml bed volume) of Sepharose-Ahx-Gly-Phe-$NHCH_2CN$ was prewashed with 12 ml of 50 mM sodium citrate buffer in water/ethanediol (2:1, v/v), pH 4.5 (elution buffer), followed by 12 ml of 50 mM sodium phosphate buffer containing 1 mM EDTA in water/ethanediol (2:1, v/v), pH 6.8 (application buffer).

Spray-dried latex (0.5 g) was dissolved in 10 ml of application buffer. The solution was clarified by filtration (0.22 μm pore size), and the protein concentration was determined. Dithiothreitol was added to 2 mM final concentration, and the mixture was kept at 0° C. for 20 min. A 80 mg portion of the latex protein was applied to the column (38 ml/ph per cm²) at 20° C., followed by 8 ml of application buffer and then 8 ml of elution buffer. 4 ml (1 bed volume) of elution buffer containing 50 mM hydroxyethyl disulphide was applied, the flow was stopped and the column was left overnight at 20° C. Elution with the hydroxyethyl disulphide solution was then resumed for a further 10 ml, before the column was re-equilibrated in application buffer. Fractions (1 ml) were collected throughout.

Active fractions from the affinity column (see above) were combined into two pools; material unretarded by the column, and material eluted in hydroxyethyl disulphide. These were applied separately to the Mono S HR 5/5 (cation-exchange) column without any further treatment. The column had been pre-equilibrated in 50 mM sodium

TABLE 1

| | Protein (mg) | Chymo-papain | Papain | PPIII | PPIV | Activity (nKat) | Specific activity (nKat/mg) | Yield (%) | Purification (fold) |
|---|---|---|---|---|---|---|---|---|---|
| Papaya latex | 5932 | 26 | 6 | 14 | 23 | 3051 | 0.514 | (100) | (1) |
| Acid treatment | 2540 | 61 | <0.03 | 21 | <0.03 | 1584 | 0.624 | 51.9 | 1.21 |
| S-Sepharose 35/100 | 689 | 100 | n.d. | <0.11 | n.d. | 630 | 0.914 | 20.6 | 1.78 |
| Sepharose-ECH-Ala-PheSc | 262 | n.d. | <0.016 | 0.02 | <0.016 | 419 | 1.602 | 13.8 | 3.12 |

Values for protein are derived from the absorbance at 280 nm: 1 mg being taken as equivalent to 2.00 $A_{280}$ units up to the acid treatment and 1.83 thereafter.
Footnote to Table 1
Values for quantities of chymopapain, papain, papaya proteinase III (PPIII) and papaya proteinase IV (PPIV) were determined by immunoassay and are expressed as percentage of total protein. Preparation of the column of Sepharose-ECH-Ala-PheSc (starting with 200 g wet weight of ECH Sepharose 4B), used for the last stage of this purification, is described under Supplementary material.
Enzymatic activity hydrolysing $Bz-DL-Arg-NHPhNO_2$ is given in nKat. Since the substrate is also hydrolysed by papain and papaya proteinase III, the yield of activity is an underestimate of the yield of chymopapain, n.d. = not determined.

Footnote to Table 1

Values for quantities of chymopapain, papain, papaya proteinase III (PPIII) and papaya proteinase IV (PPIV) were determined by immuno-assay and are expressed as percentage of total protein. Preparation of the column of Sepharose-ECH-Ala-PheSc (starting with 200 g wet weight of ECH Sepharose 4B), used for the last stage of this purification, is described under Supplementary material.

acetate/acetic acid buffer, pH 5.0, containing 1 mM EDTA, and was washed with the same buffer (1 ml/min) after application of the sample until the $A_{280}$ returned to zero. A gradient (21.5 mM Na⁺/ml) to 1M sodium acetate was then applied to the column and 1 ml fractions were collected.

Two peaks of $Bz-Arg-NHPhNO_2$-hydrolysing activity were eluted from the Sepharose-Ahx-Gly-Phe-$NHCH_2CN$ column: one that passed straight through (peak 1), and one that was bound and eluted the next day in hydroxyethyl disulphide (peak 2). Of the activity applied to the column 70% was recovered in these two peaks, 52% in peak 1 and 18% in peak 2. The capacity of the affinity column was 1–2 mg of protein/ml bed volume.

Peak 2 from the affinity column was loaded on to the Mono S HR 5/5 column of the Pharmacia f.p.l.c. system. When the dithiothreitol or hydroxyethyl disulphide had washed through, and the $A_{280}$ had returned to baseline, the proteins were eluted with a gradient of sodium acetate/acetic acid buffer, pH 5.0.

The material that had bound to the affinity column produced two major protein peaks on cation-exchange (peak 2) chromatography. Peak a, eluted at about 0.17M $Na^+$, displayed high activity against both Bz-Arg-NHPhNO$_2$ and azocasein. This protein was subsequently shown to react with a monospecific antiserum to papain and therefore represents substantially pure papain. Peak a was collected, dialysed into 1 mM EDTA, freeze-dried and stored at $-20°$ C.

EXAMPLE 5

Materials and Methods for papain digestion of whole blood, plasma and serum

All chemicals used were of analytical grade and obtained from Sigma Chemical Company (Poole, Dorset) unless otherwise indicated. Papain was obtained from E. Merck (6000 USP-U/mg; Darmstadt, Germany). Blood samples were obtained from sheep previously immunized against nortriptyline.

The progress of digestion was assessed at hourly intervals by subjecting aliquots of the incubation medium to gel filtration chromatography and SDS-gel electrophoresis according to the following protocols:

Gel chromatography: A 0.8×100 cm column of high resolution Sephacryl S-100 (Trademark; Pharmacia LKB, Uppsala, Sweden) was used to separate the immunoglobulins from Fab. The column was equilibrated at room temperature with 0.05 tool Tris-HCl buffer (pH 8.0 containing 0.01 (w/v) sodium azide. Following application of digested sample (0.2 ml), the column was eluted with the same equilibrating buffer at a flow rate of 0.3 ml/min. Fractions of 3 ml were collected. Protein peaks were identified by uv absorbance. Immunoglobulins and Fab antibody activity were assessed by an in-house enhanced fluoroimmunoassay. SDS-gel electrophoresis: aliquots (2 μl) were electrophoresed on 7.5% sodium dodecyl sulphate (SDS)-polyacrylamide gels under non-reducing conditions. Before application to the gels, samples were prepared in 50 μl sample buffer (0.5 mol tris/HCl buffer pH 7.5 containing 2% SDS, 10% glycerol and 0.01% bromophenol blue) and boiled for 5 min. A protein solution (Bio-Rad Laboratories, USA) was also run to calibrate each gel according to molecular weight markers.

After electrophoresis, the gel was stained with Coomassie blue R, dried and then photographed for permanent record.

EXAMPLE 6

Figure 6A:
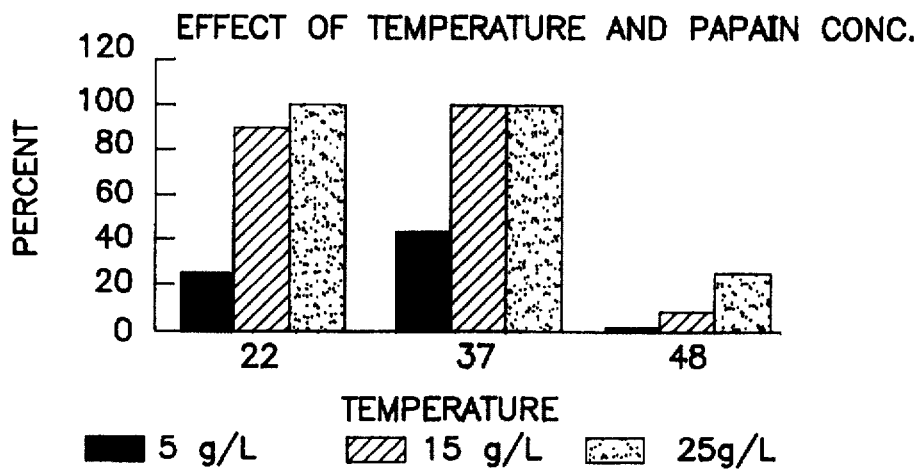
FIG. 6A–6C show the effect of papain concentration and temperature (FIG. 6A), pH (FIG. 6B), and time (FIG. 6B) on the digestion of whole blood.
Figure 6B:
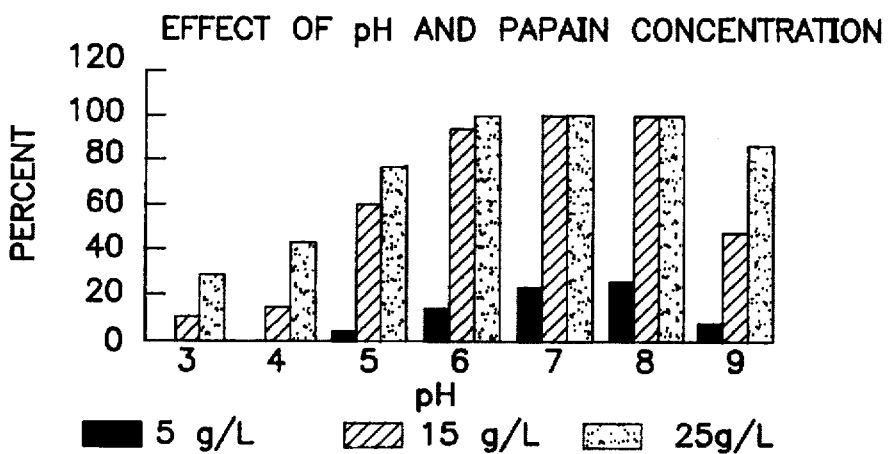
Figure 6C:
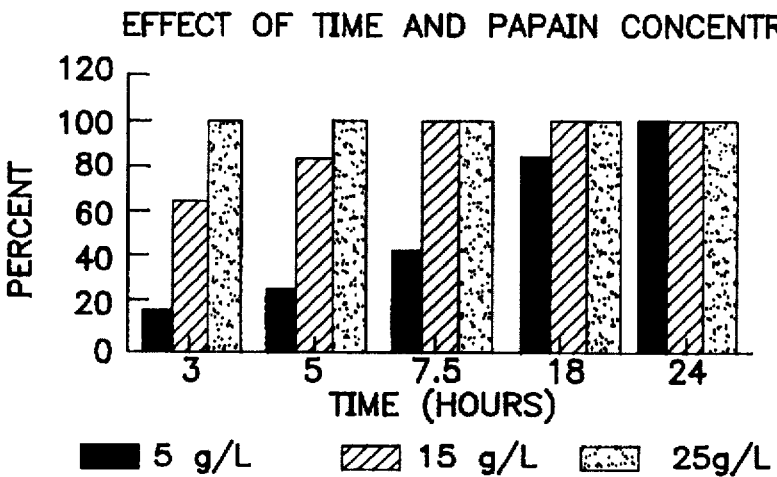

Effect of papain concentration, temperature, pH and time on digestion of whole blood The optimum conditions (temperature, pH and incubation time) for papain digestion of immunoglobulins were ascertained by a series of experiments that utilized whole blood, plasma or serum as a starting material. The main findings for whole blood are described in FIG. 6.

The optimum amount of papain to add is 15 g/l; although less could be used by increasing the incubation time, problems with haemolysis may result. There was substantially no advantage in using 25 g/l, as there was only a proportionately small increase in the amount of immunoglobulin digested.

There is little difference in activity between pH 6 and 8; pH 7.5 is preferred.

Digestion with either 15 g/l or 25 g/l is substantially complete at 5 hours. Incubation for longer than 5 hours may lead to undesirable haemolysis.

Extensive chromatographic and electrophoretic investigations have indicated that the conditions specified are suitable for digesting all classes of immunoglobulins raised to all types of immunogen.

EXAMPLE 7

Papain digestion of whole blood, plasma and serum in a closed system

The process comprises the following main stages

Brief digestion of the starting material

The starting material (whole blood, plasma and serum were successfully used), derived from sheep immunized with nortriptyline, was aseptically collected into a sterile and pyrogen-free container, conveniently a double blood pack (Baxter Health Care Ltd, Egham, Surrey). The bag where digestion takes placed may be either prefilled or injected later with a sterile preparation of papain, EDTA and L-cysteine (either powder or water-based solution are suitable). The material was mixed thoroughly but gently and incubated at 37° C. for a minimum period of 3 and a maximum of 5 hours. It is preferred if this incubation time is not extended any further because it may lead to haemolysis when whole blood is used as starting material.

Typically, for whole blood, L-cysteine (5 g) and EDTA disodium salt (7.5 g) were dissolved in 50 ml sterile saline in one compartment of a sterile double blood pack. Papain (12.5 g) was added and the mixture was allowed to stand for 10 minutes before mixing. Sheep were bled and the blood (500 ml) was directly collected into one compartment of the blood pack with gentle mixing.

Typically, for plasma, EDTA (5 g) was dissolved in 50 ml sterile saline in one compartment of a sterile double blood pack. Blood (500 ml) was collected with gentle mixing. The blood was allowed to stand for 30 minutes before centrifugation at 2500×g for 30 minutes at 4° C. Plasma was transferred to the second compartment of the double blood pack.

The second compartment contained L-cysteine (5 g) and papain (12.5 g); the mixture was allowed to stand for 10 minutes before gentle mixing.

Typically, for serum, blood (500 ml) was collected in one compartment of a sterile double blood pack and allowed to stand for 1 hour at room temperature before centrifugation at 2500×g for 30 minutes at 4° C. The serum was transferred to the second container of the double blood pack containing papain (7.5 g), EDTA (2.5 g) and L-cysteine (1.5 g). The mixture was allowed to stand for 10 minutes before mixing.

For blood, plasma and serum the digestion mixtures were incubated at 37° C. for periods ranging from 3–5 hours. The blood bag is then centrifuged at 2600×g for 45 minutes at 4° C. to remove cells (where necessary) and precipitated Fc component. The supernatant, containing the digested immunoglobulin(s) is transferred through the sealed tube to the second compartment of the double blood pack, in the case of whole blood, or from the second compartment to a fresh single or double blood pack in the case of plasma or serum.

Partial purification of digested immunoglobulins by an anion exchange chromatography The digested material was applied, without any prior treatment, onto a column of anion-exchange resin (diethylaminoethyl amine, DE52; Whatman Scientific Ltd, Maidstone, Kent) previously equilibrated with sterile phosphate buffer (50 mM, pH=7.5 ). Under these conditions, almost all (>83%) of the antibody Fab fragment is immediately eluted from the column whereas other major plasma proteins such as albumin and transferrin are bound to the matrix. The column is regenerated and sterilized by any conventional method such as treatment with sodium hydroxide.

Complete purification by affinity chromatography

The matrix used in these experiments is nortriptyline covalently attached to Sepharose 4B (Pharmacia LKB Biotechnology, Milton Keynes, Bucks) as nortriptyline had been used as the immunogen. The semi-purified material obtained from the first ion-exchange column was applied directly, without any pre-treatment, and through a sealed tube, to an affinity column to allow the binding of specific Fab. Non-specific Fab and other contaminating proteins are washed out with the equilibration buffer (phosphate buffered saline, 50 mM, pH=7.5). Specific Fab was eluted from the column by application of acidic solution containing 1% propionic acid and 5% acetonitrile (pH=2.9). It is quite possible to use other well known eluants such as acidic glycine buffer.

Strong cation exchange chromatography

SP resin (Bio-Rad Laboratories Ltd, Hemel Hempstead, Hertfordshire) was used as the final step to remove undesirable chemicals from the Fab solution eluted from the affinity column, and to concentrate the material. In addition, this step also serves as a tailored equilibration of the final product into the required medium since Fab can be eluted from this exchanger by various techniques including those that utilise an upward gradient of pH, ionic strength, or both, of the eluting buffer. The affinity-purified Fab was applied directly to the column which was pre-equilibrated with dilute hydrochloric acid solution (10 mM, pH=3). Under these conditions, Fab is bound to the ion-exchanger and can be washed extensively with the same equilibration solution. Fab was then eluted by phosphate buffered saline (50 mM, pH=8.0).

Under the specified conditions and concentrations of papain, the minimum reaction time of 3 hours was found best in terms of completeness of the digestion, retainment of the original biological activity of the antibody fragment (FIG. 12) and, whenever whole blood is used, prevention of haemolysis.

Figure 7:
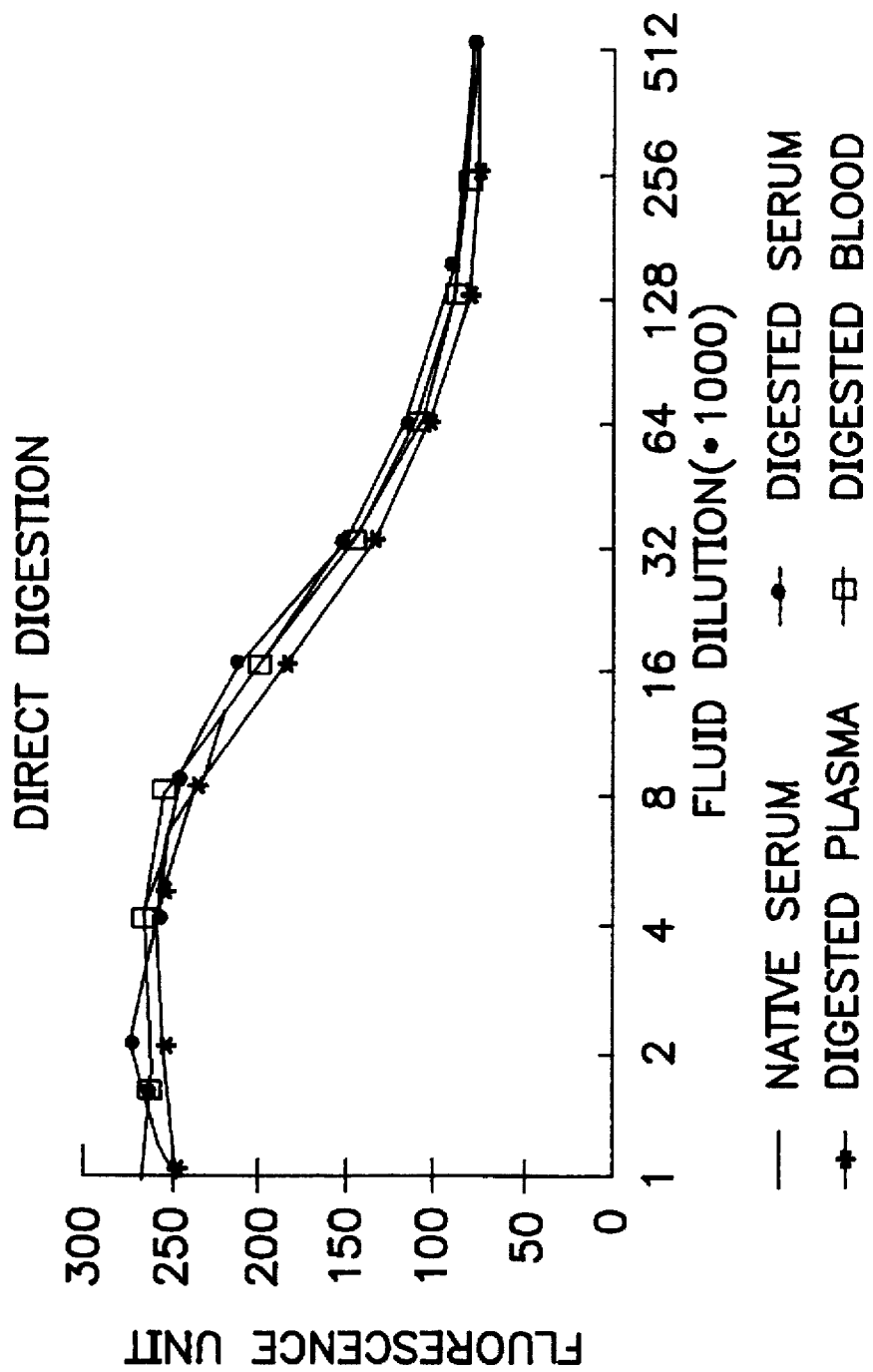
FIG. 7 shows the result of a fluoroimmunoassay showing the retainment of biological activity of digested serum, digested plasma and digested whole blood compared to native serum.

FIG. 7 shows a fluoroimmunoassay. Nortriptyline was fluorescently labelled and the binding of antibody or antibody fragment measured by the quenching of fluorescence. The results indicate that after papain digestion blood, serum and plasma have the same binding characteristics as native, untreated serum.

The use of the closed system allows the preparation of high quality and almost completely pure and sterile Fab fragments without the need for incorporating antimicrobial agents in the process. Furthermore, the conditions for each stage are arranged to negate any need for sample handling or treatment. Although these results were obtained using sheep anti-nortriptyline antiserum in either whole blood, plasma or serum, our experimental findings with antivenom antisera, and other antisera, indicate that the system is applicable to the digestion and purification of a variety of specific antibody fragments from different sources. Antibody fragments prepared in this way are particularly suitable for therapeutic use.

Figure 5:
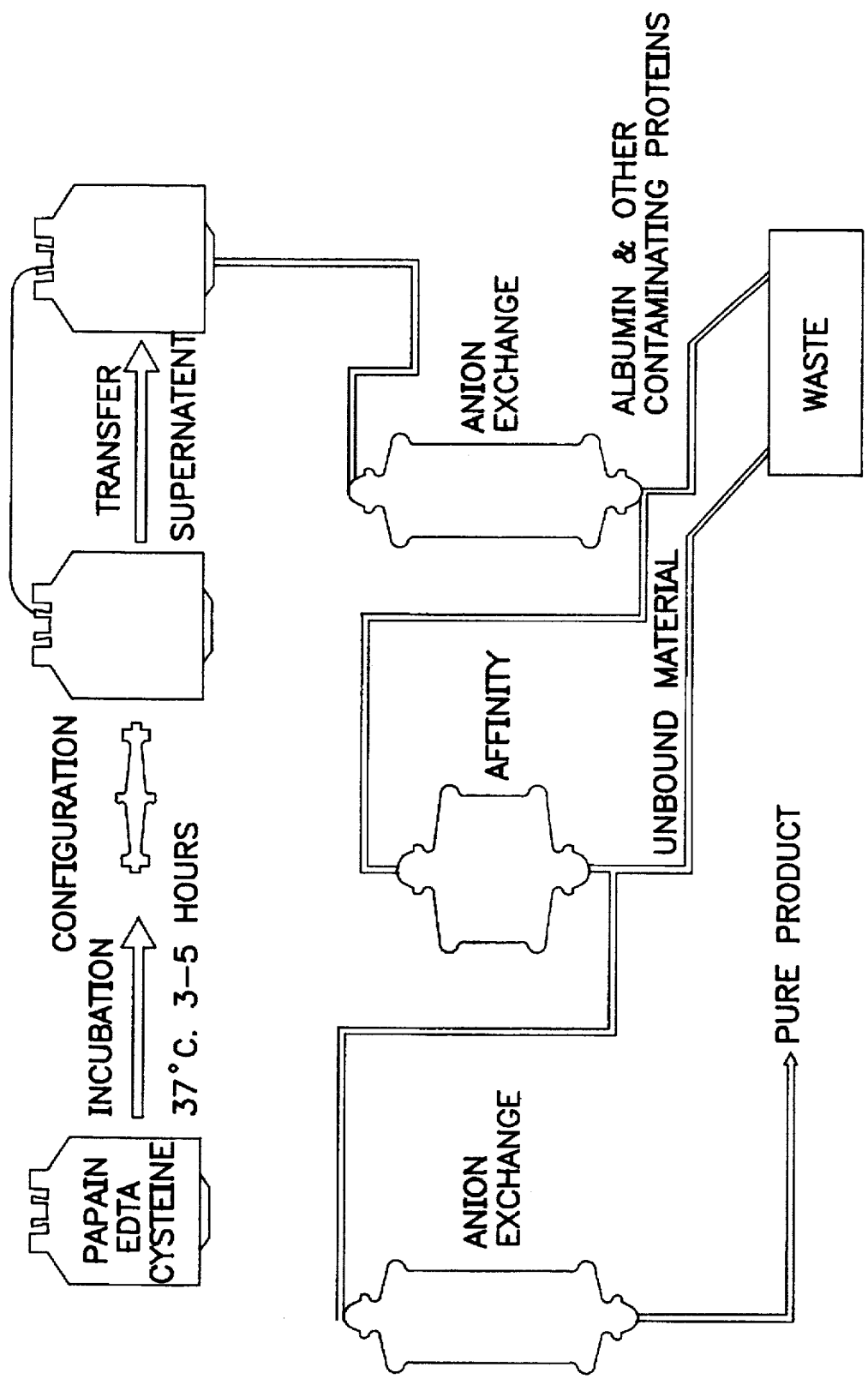
FIG. 5 shows the main components in one embodiment of the closed system for the digestion of antibodies and purification of Fab fragments.

The main components of the closed system for the digestion of antibodies and purification of Fab fragments are shown in FIG. 5.

Figure 2B:
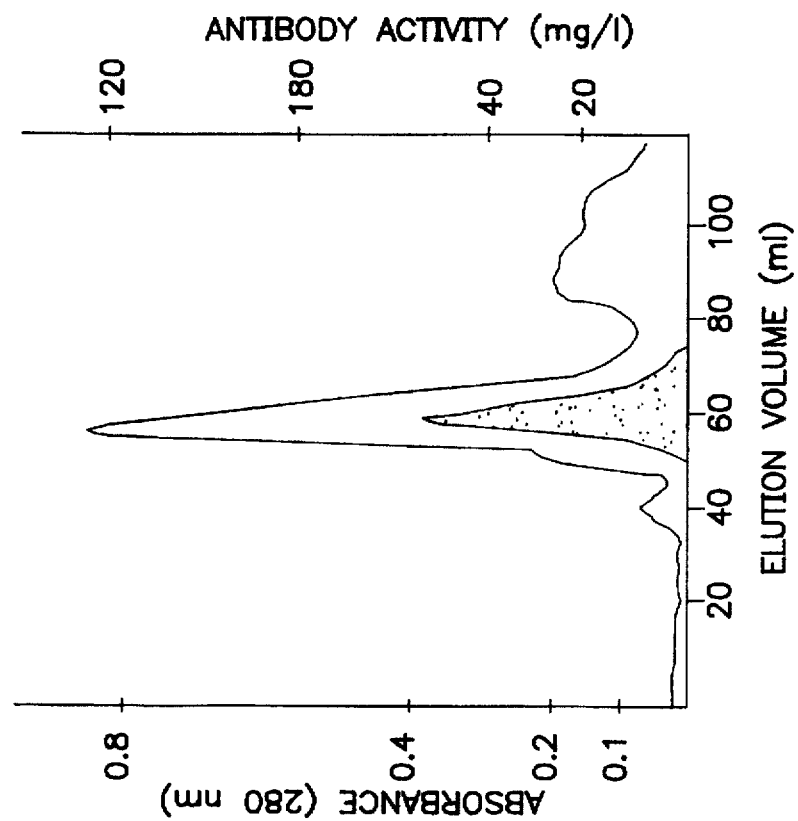
FIG. 2A and 2B show the elution profile from Sephacryl S-100 (Trademark) high resolution column chromatography of untreated plasma (FIG. 2A) and digested whole blood after centrifugation (FIG. 2B). It is apparent that the major peak of immunoglobulins present in (FIG. 3A) has almost completely disappeared in (FIG. 2A). The intact IgG peak in (FIG. 2A) and Fab peak in (FIG. 2A) are associated with the shaded area of each graph.
Figure 2A:
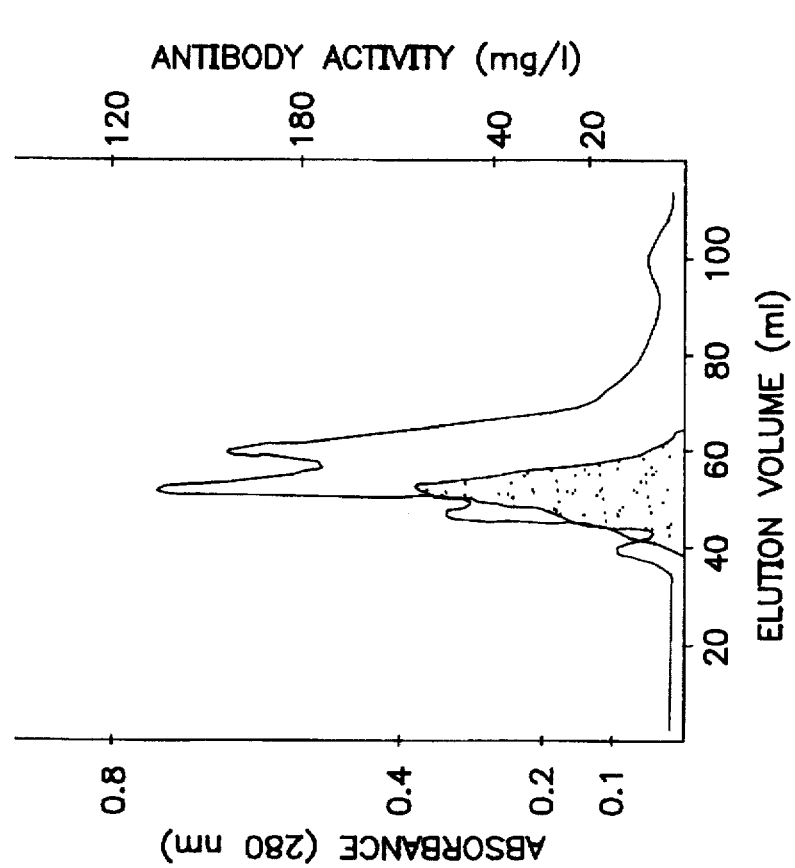
Figure 3:
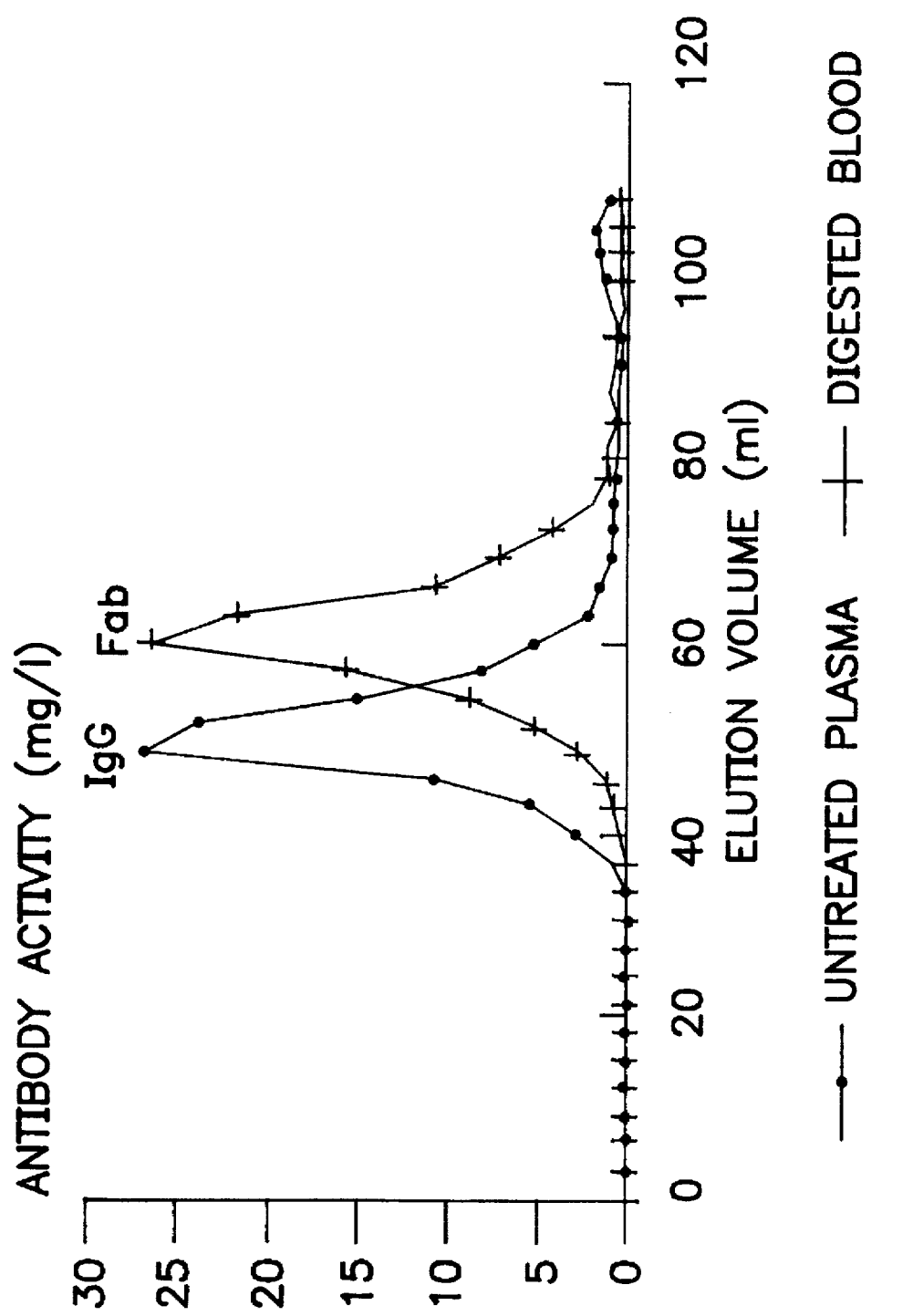
FIG. 3 shows an assessment of antibody activity in fractions obtained by gel filtration chromatography as described in FIG. 2.

With whole blood, plasma and serum the process described yielded a product which on Sephacryl S-100 showed almost complete degradation of the major protein peak containing immunoglobulins (FIG. 2). Antibody activity showed a similar shift to a peak in the expected position of Fab (FIGS. 2 and 3). FIG. 2(a) shows the elution of antibody activity (shaded region) from untreated plasma IgG elutes at approximately 50 ml elution volume. FIG. 2(a) shows the elution of antibody activity (shaded region) from digested whole blood after centrifugation. Fab elutes at approximately 60 ml elution volume.

Figure 4:
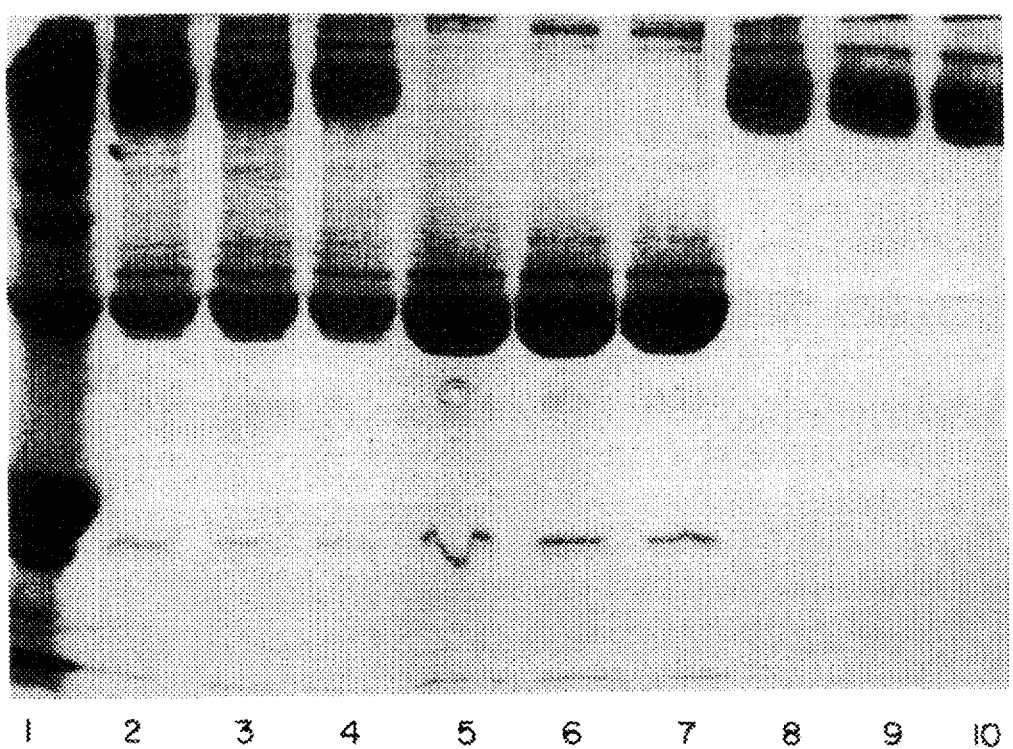
FIG. 4 shows the results of non-denaturing SDS-PAGE electrophoresis of molecular weight markers (lane 1), untreated serum (lane 2, 3, 4), digested whole blood after centrifugation (lane 5, 6, 7) and semipurified preparation of immunoglobulins (lane 8, 9, 10). Note the absence of any significant band in the gamma region for the digested product.

SDS-PAGE (FIG. 4) confirmed that complete digestion is obtained and that the end product is virtually devoid of intact immunoglobulins.

EXAMPLE 8

Alternative method of preparing Fab fragments in a closed system

Immunised sheep are bled, via the jugular vein, into sterile, pyrogen free plastic bags containing pyrogen free papain (0.2% by weight), EDTA (0.5% by weight) and cysteine (0.3% by weight). This mixture is incubated for a minimum of 18 hours at 37° C. to complete digestion of the IgG and then centrifuged (3500 rpm) to pellet the red cells and crystallized Fc fragments. A variable proportion, but not all, of the papain may precipitate at this stage and is also removed by centrifugation.

Figure 8:
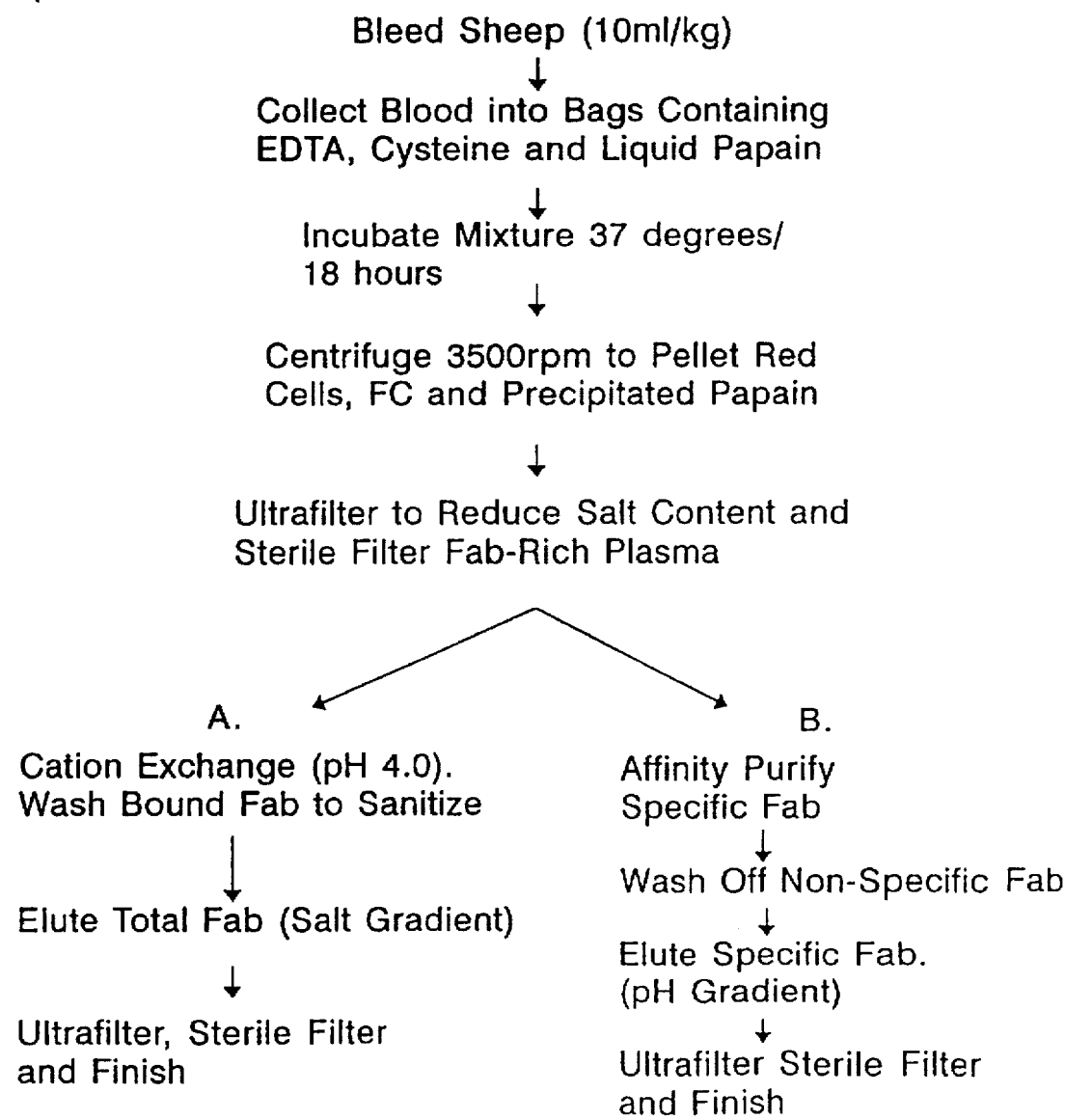
FIG. 8 shows a flow diagram for one embodiment of polyclonal antibody processing-whole blood digestion.

The supernatant from each bag is then siphoned into a separate plastic transfer bag, which, when full, is connected to an ultrafiltration system. The system is fitted with 10 kD membranes which allow the passage of low molecular weight proteins and salt but which retain Fab molecules. The Fab solution is washed with low molarity buffer (ammonium acetate, 50 mM, pH 4.0) or saline (0.9%) depending on the method of further purification. The concentration of the Fab is brought up to between 40–60 g/l and filled into plastic bags prior to further purification (see FIG. 8).

Figure 9:
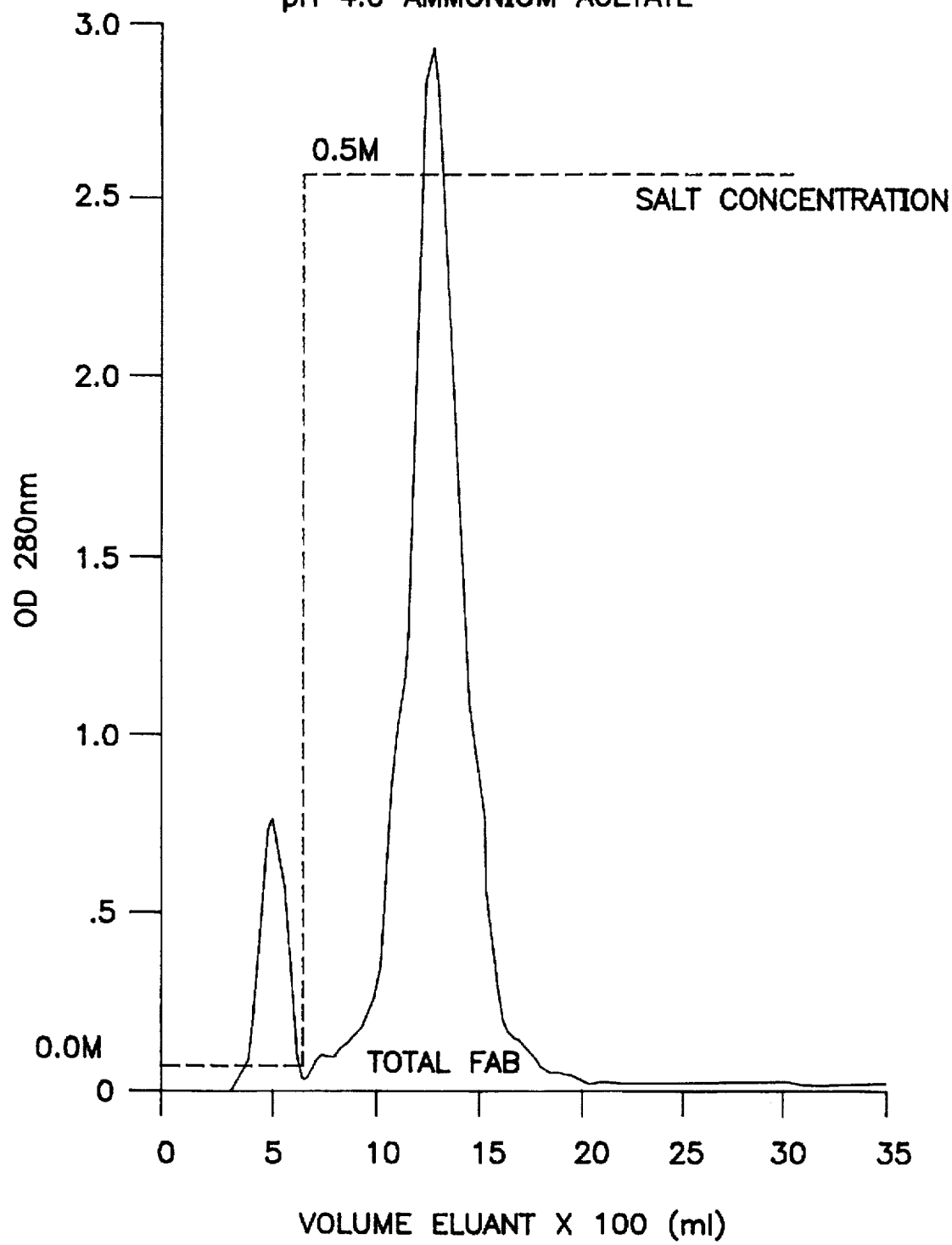
FIG. 9 shows a typical profile following cation exchange chromatography.

A: Cation Exchange Chromatography (FIG. 9).

The total Fab solution (in ammonium acetate buffer) is applied to a cation exchange column (BioRad MacroPrep S although a weaker binding column may be used) where the majority of the Fab (>80%) binds. The column, and thereby the bound Fab, is then washed with three column volumes of buffer (ammonium acetate pH 4.0) to sanitize the product and remove potential contamination by prion or virus.

Once washed, the bound total Fab is eluted by washing the column with the application buffer containing sodium chloride (0.5M). The eluted Fab is then ultrafiltered and washed with saline to remove ammonium acetate buffer, concentrated as required and pumped into a sterile plastic transfer bag. This bag may be connected directly to the filling machine. The product is terminally filtered, filled and finally filled and lyophilized.

The ion exchange column is sanitized between runs using sodium hydroxide (1.0M) and then re-equilibrated with ammonium acetate buffer ready for the next cycle.

B: Affinity Purification

Figure 10:
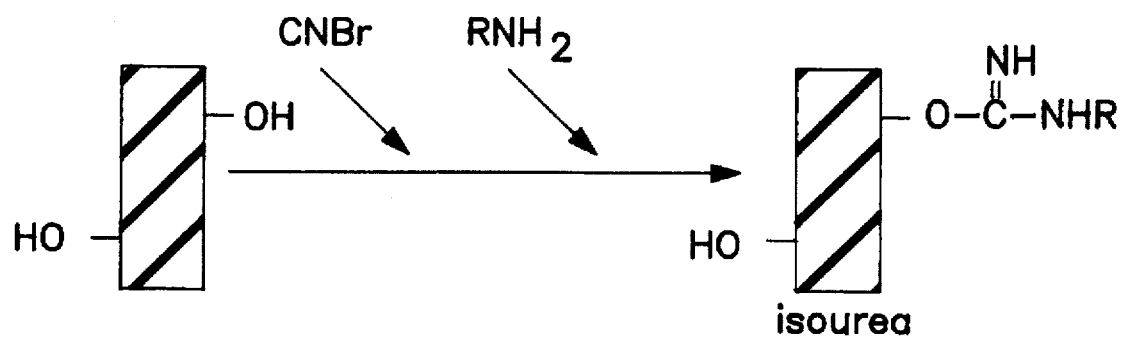
FIG. 10 shows the iso-urea linkage chemistry to agarose gels.

The Fab solution in saline is applied to an agarose affinity column comprising antigen bound via and iso-urea linkage (FIG. 10) to cyanogen-bromide activated Sepharose 4B or via an amine linkage to controlled pore glass. The Fab solution is recirculated through the column for 18 h at room temperature during which time antigen specific Fab bind to the affinity matrix ligand.

Figure 11:
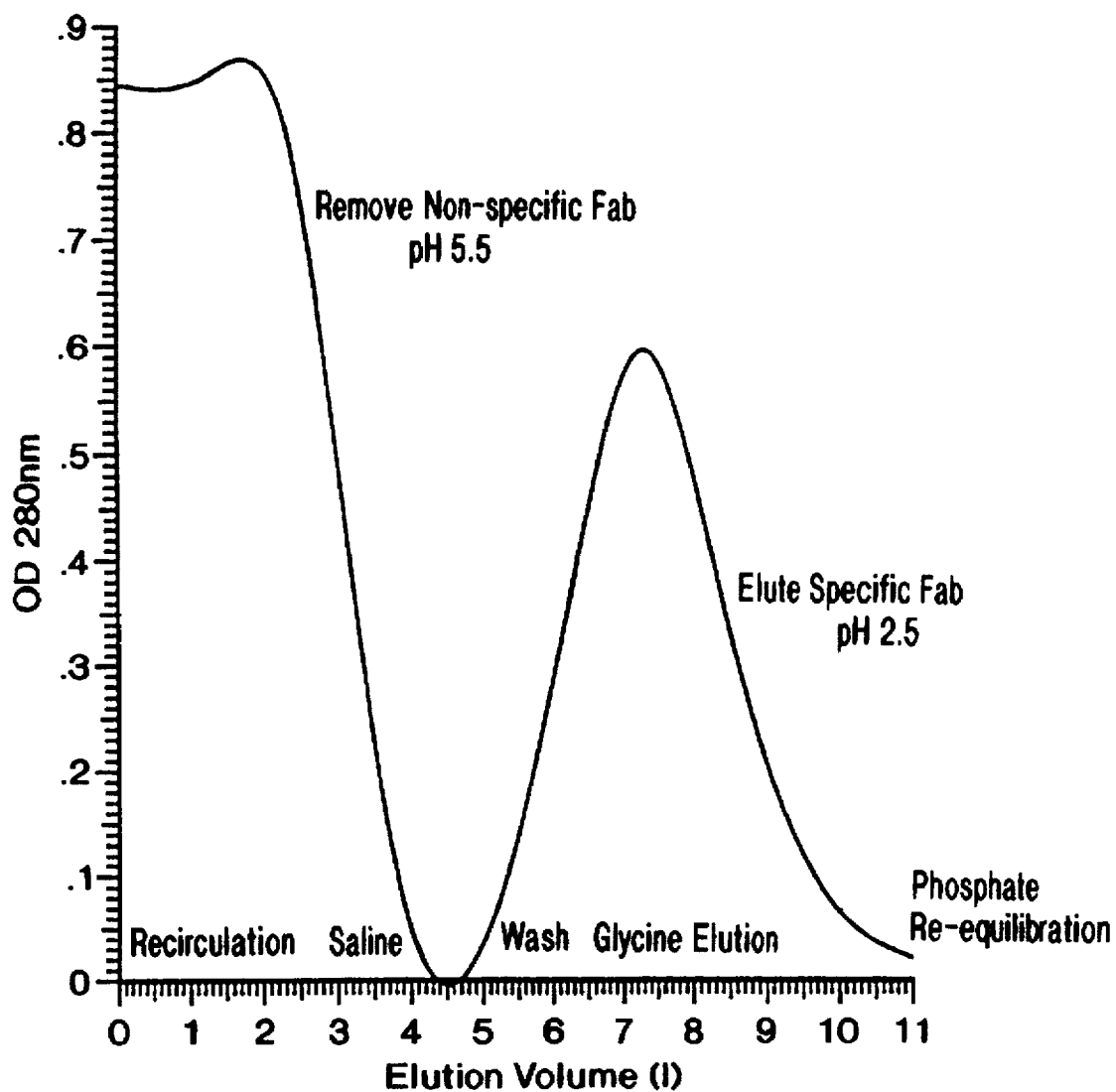
FIG. 11 shows a typical profile following affinity chromatography.

Non-specific Fab is washed from the column using saline (0.9%), the column being washed until the absorbance (280 nm) of the washings drops to the original preload value (FIG. 11).

Specific Fab is eluted by washing the column with glycine buffer (10–100 mM depending on the project, pH 2.5)

containing sodium chloride (0.9%). The eluted Fab is then finished and filled as described in schedule A.

The affinity column is re-equilibrated using phosphate buffer (pH 8.0, 10–100 mM depending on the project) and then washed with saline prior to the next cycle. The columns are sanitized between runs using guanidine hydrochloride (6.0M).

EXAMPLE 9
Immobilization of papain on cellulose and activated Sepharose
Materials Papain 30,000 USP/mg (Merck)

CNBr-activated Sepharose 4B (Pharmacia)

Cellulose microgranular CC31 (Whatman)

1,1'-carbonyldiimidazole (CDI) (Sigma)

L-cysteine (Sigma)

Acetone "AnalaR" (BDH)

Sheep IgG (Sepharose is a trademark of Pharmacia; AnalaR is a trademark of BDH Ltd)
Methods
Coupling papain to CBNr-activated Sepharose 4B To every gram of dried Sepharose 4B was added 50 mg papain (weight based on protein concentration) and at least 90 percent of the enzyme was incorporated (ie 45 mg crude papain was coupled to every gram of solid support). In order to determine the activity of the immobilized enzymes compared to their activity in free solution, an assay using N-Benzoyl-L-Arginine p-Nitroanilide (L-BAPNA) as substrate was performed. Their ability to cleave sheep IgG was then studied. Solid phase papain-(1 g) was first activated with saline containing L-cysteine and EDTA and then 450 mg sheep IgG (ratio papain to IgG 1:10) was added and the reaction was left to proceed at 37° C. for 15 hours. Then the product was separated by centrifugation and its purity checked on FPLC and SDS Page. Reusability of the coupled enzymes was also investigated: After each IgG digestion the solid phase papain was washed with saline and stored at 4° C. for reuse under the same conditions as above.
Coupling papain to 1,1'-carbonyldiimidazole (CDI)-activated cellulose Whereas the Sepharose 4B is purchased as an activated material, the cellulose must first be activated with CDI in acetone. Cellulose (10 g) was activated with CDI (1.25 g) in 50 ml acetone at ambient temperature for 60 minutes with vigorous mixing. The activated imidazole-carbamate cellulose was recovered by filtration over a glass microfibre filter, washed with three 100 ml aliquots of acetone and air-dried for 20 minutes. "Merck" papain (160 mg weight based on protein concentration) in 80 ml Na-bicarbonate buffer was added and the reaction was left to proceed at ambient temperature with mixing for 16 hours. Washing and blocking of the remaining active sites were performed according to "Pharmacia" method. About 50 percent of the enzymes were incorporated in this experiment (7 mg crude papain coupled to every gram of cellulose).

The product was assessed by: means of (L-BAPNA) assay, its ability to cleave sheep IgG and its reusability (under the same conditions as for Sepharose 4B).
Results Papain is successfully immobilized on both CNBr-activated Sepharose 4B and CDI-activated cellulose. The amount of crude enzymes coupled to cellulose was about ten times less than that coupled to Sepharose. The two behaved in similar manner when used to cleave sheep IgG giving as pure Fab as that produced in liquid phase digestions when analysed on FPLC and SDS Page. The studies of reusability and stability indicate that both supports can be reused with satisfactory results more than ten times (over 90% digestion in each run). Both showed loss of activity after about one month, a phenomenon also seen with papain from Merck in solution.

Because the cysteine proteases were covalently linked to each of the solid supports, leaching was <0.1% and the product Fab after each digestion was free of enzymes (as checked by L-BAPNA assay).

EXAMPLE 10
Alternative method for immobilization of Merck Papain 30 000 USP on microgranular cellulose powder Protein immobilization on microgranular cellulose can be achieved in two steps:

Activation of the cellulose.

Coupling of the enzyme.

In this experiment the 1,1'-Carbonyl-Diimidazole (CDI) method will be used.
Reagents Microgranular cellulose powder (grade CC 31) "Whatman Lot 2431026".

Merck Papain (grade 30 000 USP-U/mg) "Merck Lot 802 F791049".

1,1'-Carbonyl-Diimidazole (CDI) "Sigma Lot 21 H2628"
Acetone "BDH" Lot 322K19746805".

Sodium bicarbonate buffer (0.1M) containing (0.5M) sodium chloride: pH 8.

Sodium acetate buffer (0.1M) containing (0.5M) sodium chloride :pH 4.5.

Ethanolamine (0.5M) [1.5 ml Ethanolamine in 50 ml sodium bicarbonate buffer, then adjust pH to 8.
Method
A) Cellulose activation 10 g of microgranular cellulose powder is weighed into a 100 ml conical flask fitted with a ground glass stopper. (CDI) 1.25 g/50 ml acetone is added and the reaction is left to proceed at ambient temperature for 1 hour with vigorous mixing.

The activated imidazolyl-carbamate cellulose is recovered by filtration over a glass microfibre filter (Whatman GF/B, retention efficiency 1 μm), and washed with three 100 ml aliquots of acetone. The activated cellulose is then allowed to air-dry (30 rain under laminar flow) and stored in a tightly sealed container at −20 until required for protein coupling.
B) Coupling of the enzyme If the activated cellulose has been stored, it is allowed to reach room temperature. Merck papain powder (1.5 g) is dissolved in 80 ml sodium bicarbonate buffer (20 rain with mixing) and its optical density at 280 nm is measured. Using an extinction coefficient (E=2.17), the concentration of the enzyme is then determined and the equivalent of 150 mg papain is added to the activated cellulose (15 mg of papain offered to every gram of cellulose.) The coupling reaction is left to proceed for 18–20 hours at ambient temperature on an end-over-end mixer.
C) Blocking the excess active groups The mixture (cellulose+enzyme) is centrifuged for 10 min at 2000 rpm, 25° C., supernatant and solid support are separated and ethanolamine (30 ml, pH 8) is added to the solid support. Blocking is carried-out at room temperature for 2 hours after which the solid support is washed with coupling buffer followed by acetate buffer and again coupling buffer using the suction filter (G3 and Whatman GF/B). Store the enzyme-cellulose conjugate in 30 ml coupling buffer at 4°–8° C.

D) Determination of coupled papain

Enzyme coupled to the cellulose is estimated by determining the protein concentration before coupling and subtracting the protein recovered (supernatant concentration) after coupling. Papain coupled to the cellulose is assumed to be the difference between these values.

Original papain solution
* optical density=D
* concentration=C
* volume used=V

Total enzyme used: V.C=X (mg).

Supernatant after coupling
* optical density=D'
* concentration=C'
* volume recovered=V'

Enzyme recovered: V'.C'=Y (mg).

Supernatant after blocking
* optical density=D"
* concentration=C"
* volume recovered=V"

Enzyme recovered: V".C"=Z (mg).

Total enzyme recovered=Y+Z $$\% \text{ INCORPORATION} = 100 - \frac{Y+Z}{X} \cdot 100$$

EXAMPLE 11

Figure 12:
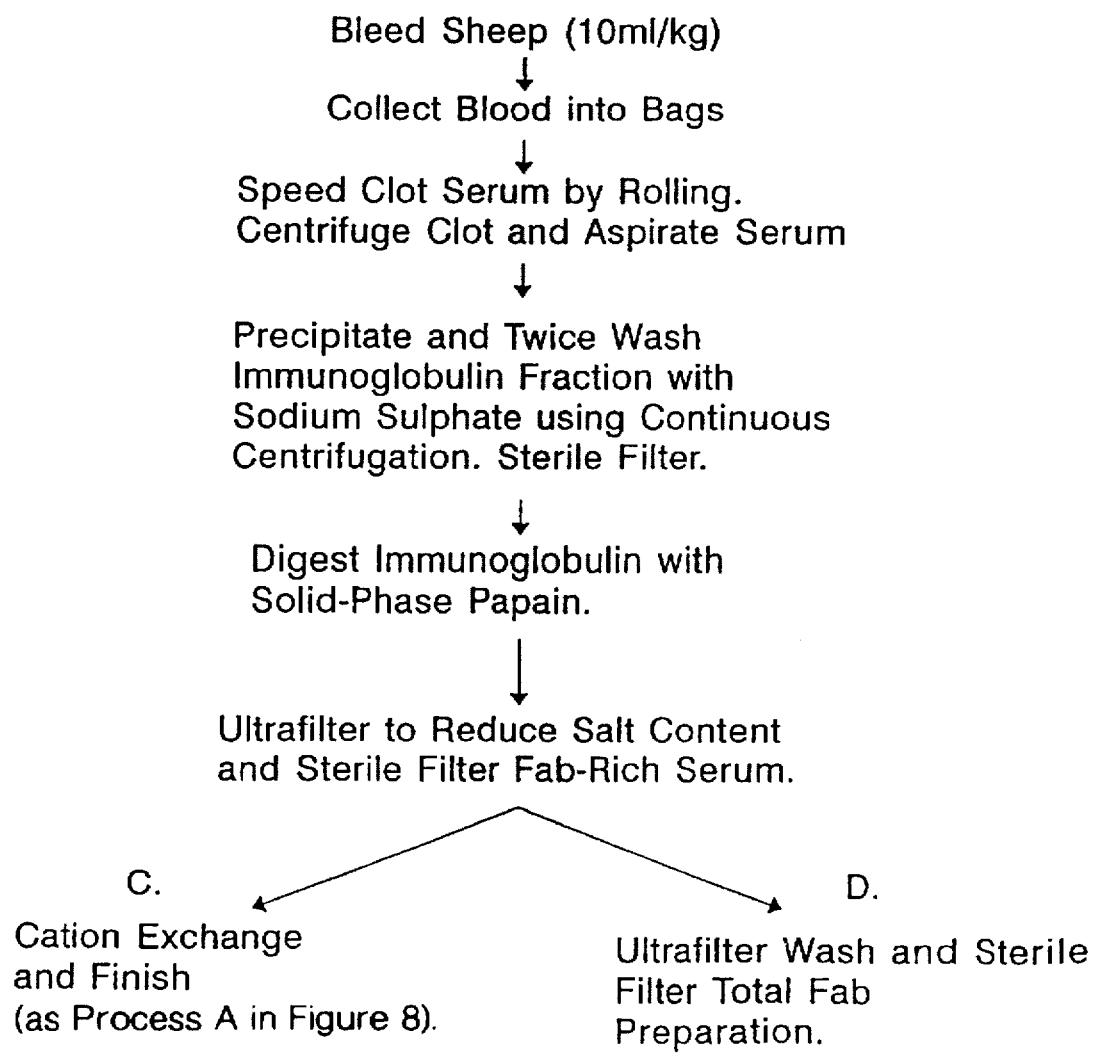
FIG. 12 shows a flow diagram for polyclonal antibody processing using "speed clotting" and digestion with immobilised papain.

Polyclonal antibody processing using "speed clotting" and digestion with immobilised papain The process is described diagrammatically in FIG. 12. Immunised sheep are bled into sterile, pyrogen free plastic bags and the serum then speed clotted by placing the bags into a cylindrical plastic former and rolling for a minimum of twenty minutes (see Example 13). After this time bags are suspended and serum siphoned off to a transfer bag. When all serum has been removed, transfer lines are clipped to prevent transfer of red cells. The serum is then sterile filtered and transferred, by peristaltic pump to a closed stainless steel mixing vessel where it is warmed to 25° C. and then mixed with an equal volume of sodium sulphate (36%, 25° C.) to precipitate the immunoglobulin fraction of the serum. The precipitate, which is predominantly IgG, is then pelleted in a continuous centrifuge and washed with two volumes of sodium sulphate (18%, 25° C.). The washed precipitate is resuspended in a half volume of saline (0.9%) and then pumped into a transfer bag to await further processing.

The IgG preparation is further digested to Fab fragments using a solid-phases papain method. Low endotoxin papain is coupled to cellulose using the method described in Example 10. A papain-cellulose slurry is then transferred, by peristaltic pump to a plastic bag and the enzyme activated by addition of EDTA (0.2%) and cysteine (2.8%) in saline (0.9%). Activation is performed for one hour at 37° C. after which time the bag is centrifuged and the supernatant removed by siphoning as above. The IgG solution is then added by peristaltic pump and the mixture incubated at 37° C.

C. Extra Pure Ion Exchange Purified Total Fab

Twice washed, solid-phase papain digested IgG is further purified using the cation-exchange chromatography step described in Example 6.

D. Total Fab Purification

The twice washed, solid-phase digested total Fab is washed with saline (0.9%) and the concentration brought up to between 50–75 g/l ready for filling and finishing.

EXAMPLE 12

Preparation of anti-TNFα Fab fragments from partially purified IgG

Sheep are immunised according to a set schedule with amounts of rhTNFα selected on the basis of dose response studies and as disclosed in Example 1. Once adequate circulating specific antibody levels have been obtained (at least 3 g/L) the sheep are bled aseptically into sterile and pyrogen-free glass bottles; clotting is accelerated by use of a roll-bottle technique; the bottles are centrifuged; and the serum is collected by aspiration in a laminar flow cabinet, subjected to 0.2 μm filtration and stored at −20° C.

Bacterial and pyrogen contamination is prevented and the product is subjected to rigorous quality control.

Antisera from different animals are pooled and their immunoglobulins precipitated at 25° C. with sodium sulphate to separate them from most other serum proteins including albumin. The immunoglobulins, which largely comprise antibodies of the IgG class, are washed with sterile sodium sulphate and resuspended in saline.

Papain digestion: The next step is cleavage of the antibodies into Fab and Fc using papain activated with cysteine and EDTA. This is carried out under conditions that ensure the complete degradation of intact IgG. The crystalline Fc is removed by centrifugation. The supernatant after papain digestion and centrifugation will contain: (1) specific Fab directed against the soluble antigen of interest; (2) non-specific Fab directed against numerous other epitopes and of no value for therapy; (3) small amounts of protein (including albumin) and other contaminants; and (4) inactivated papain.

Affinity chromatography

Affinity Purification. Affinity purification of human tumour necrosis factor (anti-TNF) Fab fragment is performed using a cross-linked agarose (Sepharose) medium to which rTNFα (recombinant human TNFα) has been bound. An iso-urea linkage is used to couple the rTNFα to the medium.

Manufacture of Agarose-rTNFα affinity column matrices

Materials

Cyanogen bromide activated Sepharose 4B (Pharmacia, Uppsala, Sweden)

rTNFα (R/D Systems Minneapolis, USA)

BPG affinity column housing (Pharmacia)

Large glass sinter funnel

Buchner flask

Vacuum pump

Glass rod

Nalgene bottle

Buffers and Solutions

All buffers must be sterile and pyrogen free (see SOP 0.2, preparation of sterile, non-pyrogenic buffers for therapeutic manufacture). Hydrochloric Acid (1 mM, 200 ml/g, ice cold) Sodium bicarbonate (0.1M, pH 8.3) containing sodium chloride (0.5M) Ethanolamine (1.0M, pH 8.0) Sodium acetate (0.1M, pH 4.0) containing sodium chloride (0.5M)

Procedure. When making columns for therapeutic manufacture, all procedures should be performed under laminar flow in class 100 conditions and all equipment should be sterile and pyrogen free.

Swelling and washing the gel: the required amount of freeze-dried Sepharose powder should be weighed out into a plastic Nalgene bottle and suspended in HCl (ice cold). The gel swells immediately and should be washed for 15 minutes on a sintered glass filter with the same solution (200 ml/g of gel). The solution should be added in several aliquots and the gel should be dried, after the final aliquot, until cracks appear in the surface.

Coupling the ligand: the TNF ligand (5 mg/g of gel to be used) should be dissolved in sodium bicarbonate buffer (0.1M, pH 8.3, 7 ml/g of gel to be used) in a plastic Nalgene bottle. Once dissolved, an aliquot (0.25% of the total) should be taken and then the air dried gel should be added, taking care not to splash the ligand solution from the bottle. The mixture should then be rotated, end over end, at 4° C. overnight.

Blocking the active groups on the gel: after coupling overnight, the gel solution should be transferred back to the glass sinter funnel and the ligand solution aspirated and collected. The gel should then be washed with 200 ml of ethanolamine. All washings should be collected.

The gel should then be transferred to a Nalgene bottle containing ethanolamine (1.0M, pH 8.0) and the mixture rotated overnight as before.

Washing the gel: the blocked gel should be transferred to the sinter funnel and the ethanolamine solution sucked off and collected. The gel should then be washed with coupling buffer (bicarbonate) followed by acetate buffer, then coupling buffer a second time. All washings should be collected.

The gel may now be transferred and packed into the column housing and washed thoroughly with saline (0.9%).

The coupling efficiency should be determined by measuring the amount of protein in the washings and comparing this with the initial ligand solution aliquot.

Columns are sanitised using guanidinium hydrochloride (6.0M) after each batch of material is completed and prior to the first addition of total Fab digest solution.

The Fab solution is circulated at a flow rate of 1 ml/minute for a minimum of two hours at 18° C.

Desorption of the rTNFα antitoxin Fab from the affinity support.

The ovine rTNFα Fab fragment bound to the support is removed by washing the column with glycine (10 mM, pH 2.5). The eluent is collected into citrate buffer (0.6M, pH 8.0:2.5% final concentration) and stored in Nalgene, 2 liter disposable collection bottles. Samples are taken for QC testing (GF FPLC, pH, protein concentration, sterility and LAL testing).

Affinity columns are re-equilibrated using phosphate buffer (10 mM, pH 7.3) until the eluant pH returns to approximately pH 5.5. The column is then equilibrated with saline (0.9%) to prepare for the next cycle.

EXAMPLE 13

Method of clotting blood ("roll-bottle" technique or "speed-clotting")

The site for venepuncture is prepared in an aseptic manner by the use of cotton wool with surgical spirit. It is important that the surgical spirit is allowed to dry before the needle is inserted to avoid problems of haemolysis.

Blood is collected from the vein as rapidly as possible into suitably prepared containers. Whilst, high grade glass bottles were used for the initial studies (Grade A Plasma Scandinava bleed bottles, Neville & Moore), the process can use commercially available plastic serum collection units.

Bottles are prepared by washing with detergent, followed by an acid rinse and finally a clean water rinse. After drying the bottles are capped with foil and dry heat sterilised (180° C., rain 6 hours) to destroy endotoxins. 10 mL of sterile, endotoxin-low physiological saline (Baxter Healthcare) is then added to each bottle under sterile laminar flow. Bottles are further foil capped and autoclaved (121° C., 20 Min). Following venepuncture, approximately 350 mL of blood is collected into each of the bottles, after puncturing the foil cap.

The bottles are immediately screwcapped and transferred to apparatus (Bellco Biotechnology, Vineland, N.J.) at ambient temperature which rolls the bottles placed on their sides. This permits maximum contact of the Hageman Factor and platelets with the inside wall of the bottles, thus initiating blood clot formation via the intrinsic pathway. The bottles are rolled for a minimum of 20 rain at approximately 12 rpm. This results in the formation of a clearly visible and distinguishable clot.

Immediately the bottles are balanced and centrifuged at 1200 rpm (Beckman J6) for 30 minutes. Following centrifugation the bottles are sprayed with industrial methylated spirits to destroy any possible surface bacterial contaminants and allowed to dry under laminar flow.

The caps are removed under laminar flow and the partitioned antiserum aspirated off the clot using a sterile aspiration needle connected to a peristaltic pump.

For therapeutic use, the aspirated antiserum is filtered through a two stage depth filtration train to 0.2 μm, into sterile pyrogen free containers. Samples are taken for Quality Control and the bulk immediately frozen to −20° C. in double skinned sterile plasma bags (Coloreed).

The whole process from blood collection to antiserum freezing can easily be completed following GMP within a normal working day.

Using good collection technique, bacterial contamination is minimised. At the centrifugation stage bacteria have been shown to adhere to red cells and are spun down. Any residual bacteria are removed by sterile depth filtration. Most importantly, the time and conditions for potential bacterial growth and endotoxin contamination are greatly reduced and controlled in comparison with conventional methods for antiserum production, involving overnight incubation often at elevated temperatures (+37° C.).

Antiserum samples have been analysed

Haemoglobin levels by spectrophotometric assay.

Fibrinogen levels by SDS PAGE electrophoresis and radial immunodiffusion.

Sterility by incubation in Tryptone Soya Broth.

Endotoxin levels by LAL gel clot assay.

I claim:

1. A method of preparing polyclonal immunoglobulin Fab fragments, said method comprising the following steps:

obtaining whole blood from an animal under aseptic conditions;

contacting said whole blood with papain or chymopapain to digest immunoglobulins;

removing cellular components from the resulting solution; and separating the resulting Fab fragments from the solution.

2. The method of claim 1, wherein said contacting, removing, and separating steps are also conducted under aseptic conditions.

3. The method of any one of claims 1 or 2, wherein said method comprises substantially purifying the Fab fragments.

4. The method of claim 3, wherein the Fab fragments are substantially purified by binding the Fab fragments to a ligand for which the Fab fragments are specific, removing unbound material, and separating the Fab fragments from the ligand.

5. The method of any one of claims 1 or 2, wherein the papain or chymopapain is immobilized on a support.

6. The method of any one of claims 1 or 2, wherein the Fab fragments bind a tricyclic antidepressant.

7. The method of claim 5, wherein the tricyclic antidepressant is nortriptyline.

8. The method of any one of claims 1 or 2, wherein the Fab fragments bind TNFα.

9. The method of any one of claims 1 or 2, wherein the papain or chymopapain is substantially pure.

* * * * *